United States Patent [19]

Doria et al.

[11] Patent Number: 4,579,847

[45] Date of Patent: Apr. 1, 1986

[54] AMINO DERIVATIVES OF BENZYLIDENE-PYRROLO[2,1-b]QUINAZOLINES USEFUL FOR TREATING CONDITIONS OF ALLERGIC ORIGIN

[75] Inventors: Gianfederico Doria, Milan; Carlo Passarotti, Gallarate; Maria L. Corno, Milan, all of Italy

[73] Assignee: Farmitalia Carlo Erba S.p.A., Milan, Italy

[21] Appl. No.: 681,694

[22] Filed: Dec. 14, 1984

Related U.S. Application Data

[63] Continuation of Ser. No. 515,646, Jul. 20, 1983, abandoned.

[30] Foreign Application Priority Data

Aug. 5, 1982 [GB] United Kingdom ............... 8222591

[51] Int. Cl.$^4$ .................. A61K 31/505; C07D 413/00
[52] U.S. Cl. ................... 514/234; 514/237; 514/267; 544/115; 544/252
[58] Field of Search ............... 544/252, 115; 514/267, 514/234, 237

[56] References Cited

U.S. PATENT DOCUMENTS

| | | | |
|---|---|---|---|
| 3,271,396 | 9/1966 | Bernstein et al. | 544/252 |
| 3,558,610 | 1/1971 | Breuer et al. | 542/442 X |
| 4,033,961 | 7/1977 | Schwender et al. | 544/252 X |
| 4,066,767 | 1/1978 | Schwender et al. | 424/251 |
| 4,123,533 | 10/1978 | Hermecz et al. | 542/442 X |
| 4,310,526 | 1/1982 | Doria et al. | 544/287 |
| 4,423,048 | 12/1983 | Kadin | 514/258 |
| 4,428,952 | 1/1984 | Doria et al. | 544/252 X |

FOREIGN PATENT DOCUMENTS

| | | |
|---|---|---|
| 2739020 | 3/1979 | Fed. Rep. of Germany . |
| 0077093 | 6/1977 | Japan . |
| 1512299 | 6/1978 | United Kingdom . |

OTHER PUBLICATIONS

Warner—Lambert Co, Belgian 847,011, Farmdoc Abstract 25274 (1977).
Farmitalia Cerba SPA, Belgian 893,694, Farmdoc Abstract 4543 K/03 12/29/82.
Boehringer Sohn CH, Belgian 849,542, Farmdoc Abstract Nippom Chemipha Co, Japan 85,096, Farmdoc Abstract 83472, 08/15/74).
Chugai Pharmaceutical KK, Japan 77093, Farmdoc Abstract 56583Y, 06/29/77.
Arndt, et al., Chemical Abstracts, vol. 67, 73732h (1967).
Kametani, et al., Chemical Abstracts, vol. 78, 97850y (1973).
Kametani, et al., Chemical Abstracts, vol. 82, 4452q (1975).
Kametani, et al., Chemical Abstracts, vol. 82, 16864p (1975).
Shakhidoyatov, et al., Chemical Abstracts, vol. 88, 7166j (1978).
Johne, et al., Chemical Abstracts, vol. 89, 24589n (1978).
Bergner, et al., Chemical Abstracts, vol. 89, 101913t (1978).
Shakhidoyatov, et al., Chemical Abstracts, vol. 94, 192253v 6/8/81.
Sharma, et al., Chemical Abstracts, vol. 97, 6605a (1982).

*Primary Examiner*—Donald G. Daus
*Assistant Examiner*—D. G. Rivers
*Attorney, Agent, or Firm*—Murray and Whisenhunt

[57] ABSTRACT

Amino derivatives of benzylidene-Pyrrolo[2,1-b] Quinazolines are provided, together with pharmaceutical compositions containing them. The compounds and the compositions have pharmaceutical utility and are particularly useful as anti allergy agents.

7 Claims, No Drawings

AMINO DERIVATIVES OF BENZYLIDENE-PYRROLO[2,1-b]QUINAZOLINES USEFUL FOR TREATING CONDITIONS OF ALLERGIC ORIGIN

This application is a continuation of Ser. No. 515,646, filed July 20, 1983, now abandoned.

DESCRIPTION

The present invention relates to new amino derivatives of benzylidene-pyrrolo[2,1-b]quinazolines and benzylidene-pyrido[2,1-b]quinazolines, to a process for their preparation and to pharmaceutical compositions containing them.

The invention provides compounds having the following general formula (I)

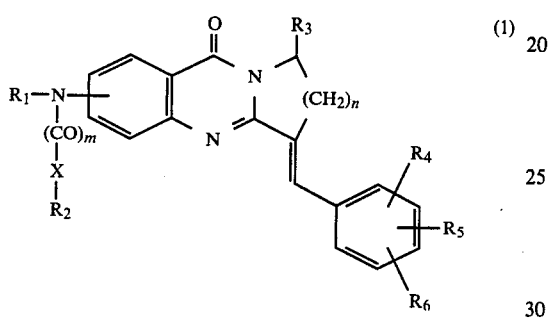

wherein
m represents zero or 1;
n represents 1 or 2;
$R_1$ represents:
 (a) hydrogen; $C_3$–$C_4$ alkenyl; or $C_1$–$C_6$ alkyl, unsubstituted or substituted by one or more substituents chosen from halogen, hydroxy and phenyl; or
 (b) formyl; or $C_2$–$C_8$ alkanoyl, unsubstituted or substituted by one or more substituents chosen from halogen, $C_1$–$C_2$ alkoxy and phenyl;
X completes a single bond or it represents:
 (a') a branched or straight $C_1$–$C_{12}$ alkylene or $C_2$–$C_{12}$ alkenylene chain unsubstituted or substituted by one or more substituents chosen from halogen and phenyl;
 (b') phenylene, unsubstituted or substituted by 1 to 4 halogen atoms;
 (c') cyclohexylene or cyclohexenylene;
$R_2$ represents:
 (a") a group —$CH_2Z$, wherein Z represents chlorine, bromine or iodine;
 (b") a group

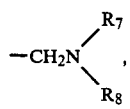

wherein each of $R_7$ and $R_8$ may be independently hydrogen or $C_1$–$C_6$ alkyl or $R_7$ and $R_8$, taken together with the nitrogen atom, form an unsubstituted N-pyrrolidinyl, morpholino or piperidino ring or a N-piperazinyl ring, which is unsubstituted or substituted by $C_1$–$C_4$ alkyl or by phenyl or by $C_1$–$C_2$ alkoxycarbonyl;
 (c") carboxy or $C_1$–$C_7$ alkoxycarbonyl, unsubstituted or substituted by a group

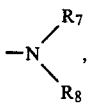

wherein $R_7$ and $R_8$ are as defined above;
$R_3$ represents a hydrogen atom or a $C_1$–$C_6$ alkyl group;
each of $R_4$, $R_5$ and $R_6$ independently represents a hydrogen or a halogen atom, $C_1$–$C_6$ alkyl, halo-$C_1$–$C_4$ alkyl, hydroxy, $C_1$–$C_6$ alkoxy, $C_3$–$C_4$ alkenyloxy, formyloxy, $C_2$–$C_8$ alkanoyloxy, carboxy, $C_1$–$C_7$ alkoxycarbonyl, wherein the alkoxy moiety is unsubstituted or substituted by a group

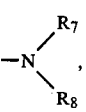

wherein $R_7$ and $R_8$ are as defined above, nitro or a group

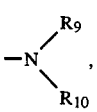

wherein each of $R_9$ and $R_{10}$ independently represents a hydrogen atom, a $C_1$–$C_6$ alkyl group, formyl or $C_2$–$C_8$ alkanoyl; or any two adjacent $R_4$, $R_5$ and $R_6$, taken together, form a $C_1$–$C_3$ alkylenedioxy group.

The scope of the invention includes also the pharmaceutically acceptable salts of the compounds of formula (I), all the possible isomers (e.g. Z and E isomers and optical isomers) and the mixtures thereof as well as the metabolites and the metabolic precursors of the compounds of formula (I).

The alkyl, alkenyl, alkylene, alkenylene, halo-alkyl, alkoxycarbonyl, alkenyloxy, alkoxy, alkanoyl and alkanoyloxy groups may be branched or straight chain groups.

The numbering used to identify the positions in the compounds of formula (I) is the conventional one, as is shown in the following Examples:

(A) when n=1:

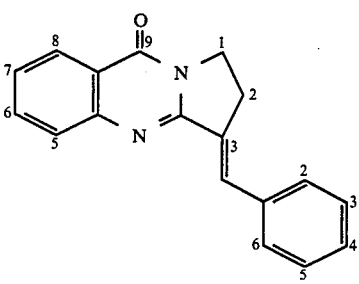

(B) when n=2:

A C$_3$–C$_4$ alkenyl group is, for example, allyl or 2-methyl-allyl.

A C$_1$–C$_6$ alkyl group is preferably a C$_1$–C$_4$ alkyl group, in particular methyl, ethyl, propyl and isopropyl.

A halogen atom is, for example, fluorine, chlorine or bromine, preferably it is fluorine or chlorine. A C$_1$–C$_7$ alkoxycarbonyl group is preferably a C$_1$–C$_5$ alkoxycarbonyl group, in particular, methoxycarbonyl and ethoxycarbonyl.

A C$_2$–C$_8$ alkanoyl group is for example acetyl, propionyl, butyryl, valeryl and isovaleryl, preferably acetyl. A halo-C$_1$–C$_4$ alkyl group is for example a C$_1$–C$_4$ alkyl group substituted by one to 3 halogen atoms, e.g. chlorine, fluorine and bromine, in particular it is trifluoromethyl. P A C$_1$–C$_6$ alkoxy group is for example a C$_1$–C$_4$ alkoxy group, in particular methoxy and ethoxy.

A C$_1$–C$_3$ alkylenedioxy group is for example methylenedioxy and ethylenedioxy.

A branched or straight C$_1$–C$_{12}$ alkylene chain is, preferably, a branched or straight C$_1$–C$_6$ alkylene chain, in particular, for example, —CH$_2$—, $$-\overset{CH_3}{\underset{CH_3}{\overset{|}{\underset{|}{C}H}}}-, \quad -\overset{CH_3}{\underset{CH_3}{\overset{|}{\underset{|}{C}}}}-, \quad -CH_2-CH_2-, \quad \overset{|}{\underset{CH_3}{C}H}-CH_2-, \quad \text{or} \quad -\overset{|}{\underset{CH_3}{C}H}-\overset{|}{\underset{CH_3}{C}H}-.$$

A branched or straight C$_2$–C$_{12}$ alkenylene chain is, preferably, a branched or straight C$_2$–C$_6$ alkenylene chain, in particular, for example, —CH=CH—, $$-\underset{CH_3}{\overset{|}{C}}=CH-, \quad \text{or} \quad -\underset{CH_3}{\overset{|}{C}}=\underset{CH_3}{\overset{|}{C}}-.$$

A C$_2$–C$_8$ alkanoyloxy group is, for example, acetoxy, propionyloxy and butyryloxy, preferably it is acetoxy.

When one or more of R$_1$, R$_7$ and R$_8$ is a C$_1$–C$_6$ alkyl group, the alkyl group is preferably a C$_1$–C$_4$ alkyl group, in particular methyl, ethyl, propyl and isopropyl.

When one or more of R$_3$, R$_4$, R$_5$ and R$_6$ is a C$_1$–C$_6$ alkyl group, the alkyl group is preferably methyl or ethyl.

When one or more of R$_4$, R$_5$ and R$_6$ is a C$_1$–C$_6$ alkoxy group, the alkoxy group is preferably methoxy, ethoxy, propoxy and isopropoxy.

More preferred compounds of the invention are the compounds of formula (I), wherein m is 1;

n is 1;

R$_1$ is hydrogen or C$_1$–C$_4$ alkyl, unsubstituted or substituted by phenyl;

X completes a single bond; or X is C$_1$–C$_6$ alkylene or C$_2$–C$_6$ alkenylene, both of them being unsubstituted or substituted by 1 up to 3 chlorine atoms;

R$_2$ is piperidinomethyl, morpholinomethyl, (1-pyrrolidinyl)-methyl or (1-piperazinyl)-methyl, wherein the piperazinyl ring is unsubstituted or substituted by C$_1$–C$_4$ alkyl, phenyl or by C$_1$–C$_2$ alkoxycarbonyl; or R$_2$ is carboxy or C$_1$–C$_5$ alkoxycarbonyl, unsubstituted or substituted by a N,N-dimethylamino or a N,N-diethylamino group;

R$_3$ is hydrogen or methyl;

each of R$_4$, R$_5$ and R$_6$, independently is hydrogen, fluorine, chlorine, C$_1$–C$_2$ alkyl, hydroxy, C$_1$–C$_3$ alkoxy, acetoxy, carboxy or any two adjacent R$_4$, R$_5$ and R$_6$, taken together, form a methylenedioxy group; and the pharmaceutically acceptable salts thereof.

Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine, tris-(hydroxymethyl)-aminomethane, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic acids, e.g. hydrochloric, hydrobromic, nitric and sulphuric acids and with organic acids, e.g. citric, tartaric, maleic, malic, fumaric, methanesulphonic and ethanesulphonic acids.

Examples of particularly preferred compounds of the invention are:

N-(3-benzylidene-9-oxo-1,2,3,9-tetrahydro-pyrrolo[2,1-b]quinazolin-6-yl)-amino-oxoacetic acid;

N-[3-(3-methyl-benzylidene)-9-oxo-1,2,3,9-tetrahydro-pyrrolo[2,1-b]quinazolin-6-yl]-amino-oxoacetic acid;

N-[3-(4-methyl-benzylidene)-9-oxo-1,2,3,9-tetrahydro-pyrrolo[2,1-b]quinazolin-6-yl]-amino-oxoacetic acid;

N-[3-(4-methoxy-benzylidene)-9-oxo-1,2,3,9-tetrahydro-pyrrolo[2,1-b]quinazolin-6-yl]-amino-oxoacetic acid;

N-[3-(3-ethoxy-benzylidene)-9-oxo-1,2,3,9-tetrahydro-pyrrolo[2,1-b]quinazolin-6-yl]-amino-oxoacetic acid;

N-[3-(4-ethoxy-benzylidene)-9-oxo-1,2,3,9-tetrahydro-pyrrolo[2,1-b]quinazolin-6-yl]-amino-oxoacetic acid;

N-[3-(4-fluoro-benzylidene)-9-oxo-1,2,3,9-tetrahydro-pyrrolo[2,1-b]quinazolin-6-yl]-amino-oxoacetic acid;

N-[3-(3-chloro-benzylidene)-9-oxo-1,2,3,9-tetrahydro-pyrrolo[2,1-b]quinazolin-6-yl]-amino-oxoacetic acid;

N-[3-(4-chloro-benzylidene)-9-oxo-1,2,3,9-tetrahydro-pyrrolo[2,1-b]quinazolin-6-yl]-amino-oxoacetic acid;

N-[3-(2,3-dimethoxy-benzylidene)-9-oxo-1,2,3,9-tetrahydro-pyrrolo[2,1-b]quinazolin-6-yl]-amino-oxoacetic acid;

N-[3-(2-methoxy-3-ethoxy-benzylidene)-9-oxo-1,2,3,9-tetrahydro-pyrrolo[2,1-b]quinazolin-6-yl]-amino-oxoacetic acid;

N-[3-(2,5-dimethoxy-benzylidene)-9-oxo-1,2,3,9-tetrahydro-pyrrolo[2,1-b]quinazolin-6-yl]-amino-oxoacetic acid;

N-[3-(2,5-dimethyl-benzylidene)-9-oxo-1,2,3,9-tetrahydro-pyrrolo[2,1-b]quinazolin-6-yl]-amino-oxoacetic acid;

N-[3-(2,6-dichloro-benzylidene)-9-oxo-1,2,3,9-tetrahydro-pyrrolo[2,1-b]quinazolin-6-yl]-amino-oxoacetic acid;

(Z)-3-[N-(3-benzylidene-9-oxo-1,2,3,9-tetrahydro-pyrrolo[2,1-b]quinazolin-6-yl)-aminocarbonyl]-2,3-dichloro-2-propenoic acid;

(E)-3-[N-(3-benzylidene-9-oxo-1,2,3,9-tetrahydro-pyrrolo[2,1-b]quinazolin-6-yl)-aminocarbonyl]-2-propenoic acid;

(Z)-3-[N-(3-benzylidene-9-oxo-1,2,3,9-tetrahydro-pyrrolo[2,1-b]quinazolin-6-yl)-aminocarbonyl]-2-propenoic acid;

N-[3-(2,4-dichloro-benzylidene)-9-oxo-1,2,3,9-tetrahydro-pyrrolo[2,1-b]quinazolin-6-yl]-amino-oxoacetic acid;

N-methyl-N-(3-benzylidene-9-oxo-1,2,3,9-tetrahydro-pyrrolo[2,1-b]quinazolin-6-yl)-amino-oxoacetic acid;

N-[3-(2-chloro-benzylidene)-9-oxo-1,2,3,9-tetrahydro-pyrrolo[2,1-b]quinazolin-6-yl]-amino-oxoacetic acid;

N-[3-(3-trifluoromethyl-benzylidene)-9-oxo-1,2,3,9-tetrahydro-pyrrolo[2,1-b]quinazolin-6-yl]-amino-oxoacetic acid;

N-[3-(3,4-dimethoxy-benzylidene)-9-oxo-1,2,3,9-tetrahydro-pyrrolo[2,1-b]quinazolin-6-yl]-amino-oxoacetic acid;

N-[3-(2,3-diethoxy-benzylidene)-9-oxo-1,2,3,9-tetrahydro-pyrrolo[2,1-b]quinazolin-6-yl]-amino-oxoacetic acid;

N-[3-(3,4,5-trimethoxy-benzylidene)-9-oxo-1,2,3,9-tetrahydro-pyrrolo[2,1-b]quinazolin-6-yl]-amino-oxoacetic acid;

N-[3-(3,4-dichloro-benzylidene)-9-oxo-1,2,3,9-tetrahydro-pyrrolo[2,1-b]quinazolin-6-yl]amino-oxoacetic acid;

N-[3-(4-carboxy-benzylidene)-9-oxo-1,2,3,9-tetrahydro-pyrrolo[2,1-b]quinazolin-6-yl]-amino-oxoacetic acid;

N-[3-(3,4-methylenedioxy-benzylidene)-9-oxo-1,2,3,9-tetrahydro-pyrrolo[2,1-b]quinazolin-6-yl]-amino-oxoacetic acid;

N-(6-benzylidene-11-oxo-6,7,8,9-tetrahydro-11H-pyrido[2,1-b]quinazolin-3-yl)-amino-oxoacetic acid;

N-(3-benzylidene-9-oxo-1,2,3,9-tetrahydro-pyrrolo[2,1-b]quinazolin-6-yl)-aminocarbonyl-acetic acid;

3-benzylidene-6-N-(3-morpholino-propionyl)-amino-1,2,3,9-tetrahydro-pyrrolo[2,1-b]quinazolin-9-one;

3-benzylidene-6-N-morpholinoacetyl-amino-1,2,3,9-tetrahydro-pyrrolo[2,1-b]quinazoline-9-one;

and the pharmaceutically acceptable salts thereof, in particular the sodium, triethanolamine and tris-(hydroxymethyl)-aminomethane salts and the hydrochlorides of the basic esters (e.g. those with 2-diethylamino-ethanol) and the $C_1$–$C_6$ alkyl esters thereof, in particular the methyl, ethyl, isopropyl and n-butyl esters.

The compounds of formula (I) can be obtained by a process comprising:

(a) reacting a compound of formula (II)

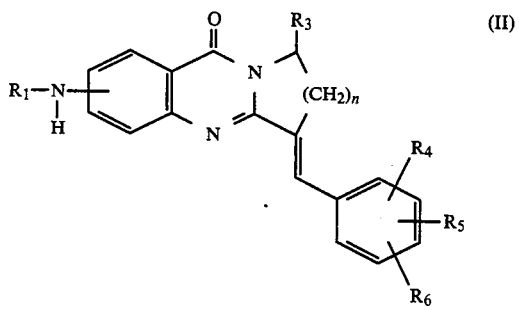

wherein n, $R_1$, $R_3$, $R_4$, $R_5$ and $R_6$ are as defined above, with a compound of formula (III)

$$R_2-X-COY \quad (III)$$

wherein X and $R_2$ are as defined above and Y represents a halogen atom, hydroxy or a group —$OCOOR_9$, wherein $R_9$ represents benzyl, phenyl or $C_1$–$C_6$ alkyl, so obtaining a compound of formula (I) wherein m is 1, or (b) reacting a compound of formula (II), as defined above, with a compound of formula (IV)

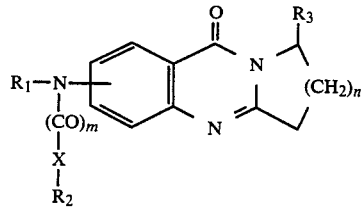

wherein X is as defined above, except a single bond, so obtaining a compound of formula (I), wherein m is 1, $R_2$ is carboxy, and X is as defined above, except a single bond; or (c) reacting a compound of formula (II), as defined above, with a compound of formula (V)

$$R_2-X-Z \quad (V)$$

wherein X, Z and $R_2$ are as defined above, so obtaining a compound of formula (I) wherein m is zero; or (d) reacting a compound of formula (VI)

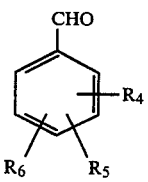

wherein m, n, X, $R_1$, $R_2$ and $R_3$ are as defined above or a salt thereof, with an aldehyde of formula (VII)

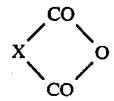

wherein $R_4$, $R_5$ and $R_6$ are as defined above; and if desired, converting a compound of formula (I) into another compound of formula (I) and/or if desired, converting a compound of formula (I) into a pharmaceutically acceptable salt and/or, if desired, converting a salt into a free compound and/or, if desired, separating a mixture of isomers into the single isomers.

In a compound of formula (III) Y is preferably chlorine, bromine, hydroxy or a group —$OCOOC_2H_5$; more preferably it is chlorine and bromine.

The reaction between a compound of formula (II) and a compound of formula (III), wherein X and $R_2$ are as defined above and Y is halogen, preferably chlorine or bromine, or a group —$OCOOR_9$, wherein $R_9$ is as defined above, may be carried out, for example, in an organic solvent such as dichloroethane, dichloromethane, chloroform, dimethylformamide, dimethylacetamide in the presence of a base such as pyridine, triethylamine, N-methyl-piperidine, N,N-dimethylaniline at a temperature varying between about 0° C. and about 100° C. preferably between 0° C. and about 40° C.

The reaction between a compound of formula (II) and a compound of formula (III), wherein X and $R_2$ are as defined above and Y is hydroxy, may be carried out, for example, in the presence of a dehydrating agent such as N,N-carbonyldiimidazole, N,N-dicyclohexylcarbodiimide, N-hydroxypiperidine, N-hydroxy-succinimide in an organic solvent such as dimethylformamide, dimethylacetamide, dichloromethane, dioxane, tetrahydrofuran, acetonitrile, at a temperature varying between 0° C. and about 120° C., preferably between room temperature and about 80° C.

The reaction between a compound of formula (II) and a compound of formula (IV) may be carried out, for example, in a solvent such as dichloromethane, dichloroethane, chloroform, tetrahydrofuran, dimethylformamide, dimethylacetamide, at a temperature varying betweeen room temperature and about 100° C., preferably between room temperature and about 70° C.

The reaction between a compound of formula (II) and a compound of formula (V) may be carried out, for example, in the presence of a base such as $Na_2CO_3$, $K_2CO_3$, NaH, $NaNH_2$ in a solvent such as dimethylformamide, dimethylacetamide, dioxane, tetrahydrofuran and their mixtures, at a temperature varying between room temperature and about 100° C.

Preferred salts of a compound of formula (VI) are those with inorganic bases such as sodium and potassium salts as well as the salts with inorganic acids e.g. hydrochloric, hydrobromic, hydroiodic and sulphuric acid.

The reaction of a compound of formula (VI) or a salt thereof with an aldehyde of formula (VII) is preferably carried out in the presence of a basic condensing agent such as sodium ethoxide, sodium methoxide, sodium hydride, sodium amide or sodium hydroxide, in a solvent selected, e.g., from the group consisting of methanol, ethanol, isopropanol, dioxane, water and their mixtures, at a temperature preferably ranging between about 0° C. and about 120° C.

A compound of formula (I) may be converted, as stated above, into another compound of formula (I) by known methods; for example, a $C_1$-$C_7$ alkoxycarbonyl group may be converted into a free carboxy group by hydrolysis, e.g. basic hydrolysis, using, for example, sodium or potassium hydroxide, in a solvent, such as water, dioxane, dimethylformamide or a lower aliphatic alcohol and their mixtures, and operating at a temperature ranging from the room temperature to about 100° C.; the same reaction may be also carried out e.g. by treatment with lithium bromide in dimethylformamide at a temperature higher than 50° C. or by treatment with hydrochloric or hydrobromic or hydroiodic or sulphuric acid in acetic acid at temperature higher than 50° C.

A free carboxy group may be converted into a $C_1$-$C_7$ alkoxycarbonyl group unsubstituted a substituted by a

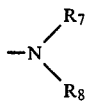

group, wherein $R_7$ and $R_8$ are as defined above, by conventional methods, for example, by reacting the acid with a suitable $C_1$-$C_7$ alkyl alcohol in the presence of a Lewis acid such as gaseous hydrochloric acid, 98% sulphuric acid, boron trifluoride etherate, at a temperature varying from room temperature and the reflux temperature.

Alternatively the esterification of a free carboxy group in a compound of formula (I) may be effected by converting the carboxylic acid into the corresponding halocarbonyl, preferably chlorocarbonyl, derivative, by reaction, e.g. with the desired acid halide, for example oxalyl chloride, thionyl chloride, $PCl_3$, $PCl_5$ or $POCl_3$, either in the absence of solvents or in an inert organic solvent such as benzene, toluene, xylene, dioxane, dichloroethane, methylene chloride or tetrahydrofuran, at a temperature ranging preferably from about 0° C. to about 120° C., and then reacting the resulting halocarbonyl derivative with a suitable $C_1$-$C_7$ alkyl alcohol in an inert solvent such as benzene, toluene, xylene, dioxane, dichloroethane, methylene chloride or tetrahydrofuran, at temperatures varying between about 0° C. and about 120° C., preferably in the presence of a base such as triethylamine or pyridine.

Furthermore a compound of formula (I) wherein $R_1$ is hydrogen may be converted into a compound of formula (I) wherein $R_1$ is $C_3$-$C_4$ alkenyl or $C_1$-$C_6$ alkyl, unsubstituted or substituted as defined above, for example, by reaction with a suitable $C_3$-$C_4$ alkenyl halide or $C_1$-$C_6$ alkyl halide, unsubstituted or substituted as defined above, in the presence of a base such as $Na_2CO_3$, $K_2CO_3$, NaH, $NaNH_2$, in a solvent such as dimethylformamide, dimethylacetamide, dioxane, tetrahydrofuran and their mixtures, at a temperature varying between room temperature and about 100° C.

A compound of formula (I) wherein $R_1$ is hydrogen may be converted into a compound of formula (I) wherein $R_1$ is formyl by heating with formic acid at a temperature varying between about 50° C. and about 100° C. A compound of formula (I) wherein $R_1$ is hydrogen may be converted into a compound of formula (I) wherein $R_1$ is $C_2$-$C_8$ alkanoyl, unsubstituted or substituted as defined above, by reaction, for example, with a suitable $C_2$-$C_8$ alkanoyl halide or anhydride in the presence of a base such as pyridine or triethylamine either in a solvent such as dimethylformamide, dioxane, tetrahydrofuran or without a solvent, at a temperature varying between about 50° C. and about 150° C.

A compound of formula (I) wherein m is zero and $R_1$ is formyl or $C_2$-$C_8$ alkanoyl, unsubstituted or substituted as defined above, may be converted into a compound of formula (I), wherein m is zero and $R_1$ is hydrogen, e.g., by acid hydrolysis using, for example, hydrochloric, hydrobromic or hydroiodic acid in aqueous solution in the presence, if necessary, of an organic cosolvent such as dioxane or acetic acid, operating at a temperature varying between room temperature and reflux temperature or by basic hydrolysis, using, for example, sodium hydroxide or potassium hydroxide in aqueous solution in the presence, if necessary, of an organic cosolvent such as dioxane or a lower alkyl alcohol, operating at a temperature varying between room temperature and reflux temperature.

A compound of formula (I) wherein $R_2$ is a group —$CH_2Z$, wherein Z is a as defined above, may be converted into a compound of formula (I) wherein $R_2$ is a group

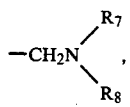

wherein $R_7$ and $R_8$ are as defined above, by reaction with a compound of formula

wherein $R_7$ and $R_8$ are as defined above, in an inert organic solvent such as dioxane, dimethyformamide, dimethylacetamide, at a temperature varying between the room temperature and the reflux temperature, preferably between the room temperature and about 100° C.

Also the optional salification of a compound of formula (I) as well as the conversion of a salt into the free compound and the separation of a mixture of isomers into the single isomers may be carried out by conventional methods.

For example the separation of a mixture of optical isomers into the individual isomers may be carried out by salification with an optically active base and subsequent fractional crystallization.

Thus, the separation of a mixture of geometric isomers may be carried out, for example, by fractional crystallization.

The compounds of formula (II), wherein $R_1$ is hydrogen, may be prepared, for example, by reducing a compound of formula (VIII)

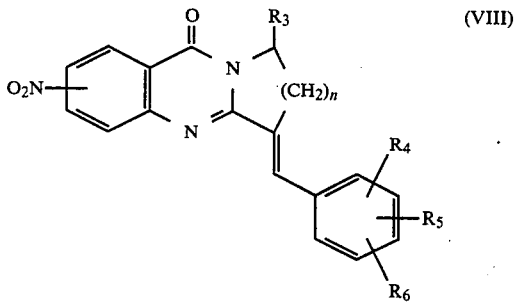

wherein n, $R_3$, $R_4$, $R_5$ and $R_6$ are as defined above, with a suitable reducing agent such as stannous chloride or sodium borohydride. The reduction of a compound of formula (VIII) with stannous chloride may be carried out, for example, in concentrated hydrochloric acid, using if necessary an organic cosolvent such as acetic acid, dioxane, tetrahydrofuran, at a temperature varying between room temperature and the reflux temperature, preferably between room temperature and about 60° C.

The reduction of a compound of formula (VIII) with sodium borohydride may be carried out, for example, in $C_1$–$C_4$ aliphatic alcohols, preferably isopropyl alcohol, tetrahydrofuran, dimethylformamide, dimethylacetamide, water and their mixtures, operating at a temperature varying between room temperature and about 60° C.

The compounds of formula (II) wherein $R_1$ is formyl or a group of $C_2$–$C_8$ alkanoyl, unsubstituted or substituted as defined above, may be prepared, for example, by reacting a compound of formula (II) wherein $R_1$ is hydrogen, respectively, with formic acid at a temperature varying between about 50° C. and about 100° C. or with a suitable $C_2$–$C_8$ alkanoyl halide or anhydride in the presence of a base such as pyridine or triethylamine either in a solvent such as dimethylformamide, dioxane, tetrahydrofuran or without a solvent, at a temperature varying between about 50° C. and about 150° C.

The compounds of formula (II) wherein $R_1$ is a group $C_3$–$C_4$ alkenyl or $C_1$–$C_6$ alkyl, unsubstituted or substituted as defined above, may be prepared, for example, by reacting a compound of formula (II), wherein $R_1$ is formyl or $C_2$–$C_8$ alkanoyl, unsubstituted or substituted as defined above, with a suitable $C_3$–$C_4$ alkenyl halide or $C_1$–$C_6$ alkyl halide, in the presence of a base such as $Na_2CO_3$, $K_2CO_3$, NaH, $NaNH_2$ in a solvent such as dimethylformamide, dimethylacetamide, dioxane, tetrahydrofuran and their mixtures, at a temperature varying between room temperature and about 100° C., and then hydrolyzing the formyl or $C_2$–$C_8$ alkanoyl moiety e.g. by treatment with a mineral acid such as hydrochloric, hydrobromic or hydroiodic acid in aqueous media at a temperature varying between room temperature and about 100° C.

The compounds of formula (VI) may be prepared, for example, by reacting a compound of formula (IX)

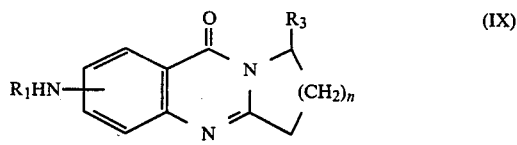

wherein n, $R_1$ and $R_3$ are as defined above, with a compound of formula (III), (IV) or (V), so obtaining respectively compounds of formula (VI), wherein m is 1; or m is 1, $R_2$ is carboxy and X is as defined above, except a single bond; or m is zero.

The reaction between a compound of formula (IX) and a compound of formula (III), (IV) or (V) may be carried out, for example, using the same experimental conditions as described above for the reaction between a compound of formula (II) and a compound of formula (III), (IV) or (V).

Alternatively the compounds of formula (VI), wherein $R_1$ is $C_3$–$C_4$ alkenyl or $C_1$–$C_6$ alkyl, unsubstituted or substituted as defined above, may be prepared, for example, by reacting a compound of formula (VI) wherein $R_1$ is hydrogen with a suitable $C_3$–$C_4$ alkenyl halide or $C_1$–$C_6$ alkyl halide, in the presence of a base such as $Na_2CO_3$, $K_2CO_3$, NaH, $NaNH_2$ in a solvent such as dimethylformamide, dioxane, tetrahydrofuran and their mixtures, at a temperature varying between room temperature and about 100° C.

The compounds of formula (VIII) may be prepared, for example, by reacting a compound of formula (X)

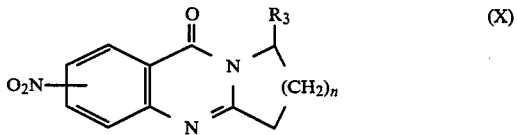

wherein n and $R_3$ are as defined above, with an aldehyde of formula (VII), using the same experimental conditions described above for the reaction between a compound of formula (VI) and an aldehyde of formula (VII).

The compounds of formula (IX) wherein $R_1$ is hydrogen may be prepared, for example, by treatment of a compound of formula (X) with a reducing agent such as stannous chloride or sodium borohydride as described above for the reduction of the compounds of formula (VIII).

The compounds of formula (IX) wherein $R_1$ is different from hydrogen may be prepared, for example, from the compounds of formula (IX) wherein $R_1$ is hydrogen, using the same chemical processes described above for the preparation of the compounds of formula (II) wherein $R_1$ is different from hydrogen.

The compounds of formula (X) may be prepared by known methods, for example, according to the methods described in published UK Patent Application No. 2103207A.

The compounds of formula (III), (IV), (V) and (VII) are known compounds and may be prepared by conventional methods: in some cases they are commercially available products.

The compounds of formula (I) have antiallergic activity and are therefore useful in the prevention and treatment of all the affections of allergic origin, e.g. bronchial asthma, allergic rhinitis, hay fever, urticaria and dermatosis. The antiallergic activity of the compounds of the invention is shown, e.g., by the fact that they are active in the following biological tests:

in vitro (1) test of A 23187 induced SRS production from rat peritoneal cells, according to M. K. Bach and J. R. Brashler (J. Immunol., 113, 2040, 1974);
(2) test of antigen induced SRS production from guinea-pig chopped lung, according to W. E. Brocklehurst (J. Physiol., 151, 416, 1960);

in vivo (3) test of the IgG mediated passive peritoneal anaphylaxis in the rat, according to H. C. Morse, K. J. Bloch and K. F. Austen (Journal Immunology, 101, 658, (1968); and
(4) test of the IgE mediated passive cutaneous anaphylaxis (PCA) in the rat, according to A. M. J. N. Blair (Immunology, 16, 749, 1969).

The results of these biological tests show that the compounds of the invention are active, for example, as inhibitors of the immunological release of allergic mediators, e.g. histamine, from the mast cells and as inhibitors of the production and/or release of anaphylactic mediators such as "slow reacting substances" (SRS) in the peritoneal and the pulmonary system, induced by challenge with an ionophore or with an antigen.

An important property of the compounds of this invention is that they are active as antiallergic agents also when administered orally.

As preferred example of compound having antiallergic activity the following can be mentioned:
N-(3-benzylidene-9-oxo-1,2,3,9-tetrahydro-pyrrolo[2,1-b]quinazolin-6-yl)-amino-oxoacetic acid.

In view of their high therapeutic index the compounds of the invention can be safely used in medicine.

For example, the approximate acute toxicity ($LD_{50}$) of the compound:
N-(3-benzylidene-9-oxo-1,2,3,9-tetrahydro-pyrrolo[2,1-b]quinazolin-6-yl)-amino-oxoacetic acid,
in the mouse, determined with single administration of increasing doses and measured on the seventh day after the treatment is per os higher than 800 mg/kg.

Analogous toxicity data have been found for the other compounds of the invention.

The compounds of the invention may be administered to humans in conventional manner, for instance, orally or parenterally at a daily dosage preferably from about 0.5 to about 15 mg/kg, or by inhalation, preferably at a daily dosage from about 0.5 to about 100 mg, preferably 0.5 to 25 mg, or by topical application, (for example for the treatment of urticaria and dermatosis), e.g. by a cream containing about from 0.5 to 5 mg, preferably 1-2 mg, of the active principle per 100 mg of cream.

The nature of the pharmaceutical compositions containing the compounds of this invention in association with pharmaceutically acceptable carriers or diluents will, of course, depend upon the desired route of administration.

The compositions may be formulated in the conventional ways with the usual ingredients. For example, the compounds of the invention may be administered in the form of aqueous or oily solutions or suspensions, aerosols, as well as powders, tablets, pills, gelatine capsules, syrups, drops, suppositories, or creams, or lotions for topical use.

Thus, for oral administration, the pharmaceutical compositions containing the compounds of this invention, are preferably tablets, pills or gelatine capsules which contain the active substance together with diluents, such as lactose, dextrose, sucrose, mannitol, sorbitol, cellulose; lubricants, for instance, silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs, sweeteners; wetting agents such as lecithin, polysorbates, laurylsulphates; and, in general, non-toxic and pharmacologically inactive substances used in pharmaceutical formulations.

Said pharmaceutical preparations may be manufactured in known manner, for example, by means of mixing, granulating, tabletting, sugar-coating, or film-coating processes.

For the treatment of allergic asthma, the compounds of the invention are also administered by inhalation. For such use, suitable compositions may comprise a suspension or solution of the active ingredient, preferably in the form of a salt, such as the sodium salt or the salt with triethanolamine or with tris-(hydroxymethyl)-aminomethane, in water, for administration by means of a conventional nebulizer.

Alternatively, the compositions may comprise a suspension or a solution of the active ingredient in a conventional liquified propellant, such as dichlorodifluoromethane or dichlorotetrafluoroethane to be administered from a pressurized container, i.e., an aerosol dispenser.

When the medicament is not soluble in the propellant, it may be necessary to add a co-solvent, such as, ethanol, dipropylene glycol, isopropyl myristate, and/or surface-active agent to the composition, in order to suspend the medicament in the propellant medium and such surface-active agents may be any of those commonly used for this purpose, such as non-ionic surface-active agents, e.g., lecithin.

The compounds of the invention may also be administered in the form of powders by means of a suitable insufflator device and in this case the fine particle sized powders of the active ingredients may be mixed with a diluent material such a lactose.

Furthermore, the compounds of this invention may also be administered by intradermal or intravenous injection in the conventional manner.

In addition to the internal administration, the compounds of this invention may find use in compositions for topical application, e.g., as creams, lotions or pastes for use in dermatological treatments.

For these compositions the active ingredient may be mixed with conventional oleaginous or emulsifying excipients. The following examples illustrate but do not limit the present invention.

EXAMPLE 1

6-amino-3-benzylidene-1,2,3,9-tetrahydro-pyrrolo[2,1-b]quinazoline-9-one, m.p. 268°–270° C. (3.1 g), was reacted with ethyl oxalyl chloride (3.2 g) in dimethylacetamide (30 ml) in the presence of pyridine (3 ml) at room temperature for 16 hours.

The reaction mixture was then diluted with ice water and the precipitate was filtered and washed with water: crystallization from dimethylformamide gave N-(3-benzylidene-9-oxo-1,2,3,9-tetrahydro-pyrrolo[2,1-b]quinazolin-6-yl)-amino-oxoacetic acid, ethyl ester, m.p. 248°–250° C. (3 g), which was dissolved in dimethylformamide (150 ml) and treated with 5% aqueous NaOH (150 ml) at room temperature for 5 hours.

The precipitate, N-(3-benzylidene-9-oxo-1,2,3,9-tetrahydro-pyrrolo[2,1-b]quinazolin-6-yl)-amino-oxoacetic acid, sodium salt, m.p. >300° C., was filtered and washed with water, then it was dissolved in formic acid and the solution was diluted with water to give a precipitate which was filtered and washed with water until netural. Crystallization from formic acid gave 1.4 g of N-(3-benzylidene-9-oxo-1,2,3,9-tetrahydro-pyrrolo[2,1-b]quinazolin-6-yl)-amino-oxoacetic acid, m.p. 220°–225° C., NMR (DMSO d6) δ ppm: 3.22 (m) (2H, C-2 protons), 4.11 (m) (2H, C-1 protons), 7.25–7.80 (m) (6H, —CH= and phenyl protons), 7.75 (dd) (1H, C-7 -proton), 8.02 (d) (1H, C-8 proton), 8.20 (d) (1H, C-5 proton), 11.0 (bs) (1H, —NH—CO—).

By proceeding analogously the following alkyl esters and acids were prepared:

N-(6-benzylidene-11-oxo-6,7,8,9-tetrahydro-11H-pyrido[2,1-b]quinazolin-3-yl)-amino-oxoacetic acid, ethyl ester, m.p. 193°–195° C.;

N-(6-benzylidene-11-oxo-6,7,8,9-tetrahydro-11H-pyrido[2,1-b]quinazolin-3-yl)-amino-oxoacetic acid, m.p. 350° C. dec., NMR (CF$_3$COOD+DMSO d6) δ ppm: 2.14 (m) (2H, C-8 protons), 3.05(m) (2H, C-7-protons), 4.16 (m) (2H, C-9 protons), 7.58 (m) (3H) and 7.74 (m) (2H) and 8.05 (m) (2H) (—CH=, phenyl protons and C-2proton), 8.33 (d) (1H, C-1 proton), 8.78 (bs) (1H, C-4 proton);

N-(3-benzylidene-1-methyl-9-oxo-1,2,3,9-tetrahydro-pyrrolo[2,1-b]quinazolin-6-yl)-amino-oxoacetic acid, ethyl ester, m.p. 232°–235° C.;

N-(3-benzylidene-1-methyl-9-oxo-1,2,3,9-tetrahydro-pyrrolo[2,1-b]quinazolin-6-yl)-amino-oxoacetic acid, m.p. 221°–225° C.;

N-(3-benzylidene-9-oxo-1,2,3,9-tetrahydro-pyrrolo[2,1-b]quinazolin-7-yl)-amino-oxoacetic acid, ethyl ester, m.p. 270°–272° C.; and N-(3-benzylidene-9-oxo-1,2,3,9-tetrahydro-pyrrolo[2,1-b]quinazoline-7-yl)-amino-oxoacetic acid, m.p. 239°–242° C., NMR (DMSO d6) δ ppm: 3.24 (m) (2H, C-2 protons), 4.17 (t) (2H, C-1 protons), 7.33–7.78 (m) (7H, —CH=, C-5 proton and phenyl protons), 8.10 (dd) (1H, C-6 proton), 8.65 (d) (1H, C-8 proton), 10.99 (s) (1H, —NH—CO—).

EXAMPLE 2

6-amino-3-benzylidene-1,2,3,9-tetrahydro-pyrrolo[2,1-b]quinazoline-9-one (2.5 g) was reacted with 3-carbometoxy propionyl chloride (1.95 g) in dimethylacetamide (110 ml) in the presence of pyridine (2 ml) at room temperature for 18 hours. The reaction mixture was then diluted with ice water and the precipitate was filtered and washed with water to give 3-[N-(3-benzylidene-9-oxo-1,2,3,9-tetrahydro-pyrrolo[2,1-b]quinazolin-6-yl)-aminocarbonyl]-propanoic acid methyl ester, m.p. 288°–291° C. (3.3 g) which was dissolved in dimethylformamide (120 ml) and treated with 5% aqueous NaOH (32.5 ml) at room temperature for 3 hours. The precipitate, 3-[N-(3-benzylidene-9-oxo-1,2,3,9-tetrahydro-pyrrolo[2,1-b]quinazolin-6-yl)-aminocarbonyl]-propanoic acid, sodium salt, m.p. >300° C., was filtered and washed with water, then it was dissolved in formic acid and the solution was diluted with water to give a precipitate which was filtered and washed with water until neutral to give 2.07 g of 3-[N-(3-benzylidene-9-oxo-1,2,3,9-tetrahydro-pyrrolo[2,1-b]quinazolin-6-yl)-aminocarbonyl]-propanoic acid, m.p. 250°–255° C. dec., NMR (DMSO d6) δ ppm., 2.62 (bs) (4H, —COCH$_2$CH$_2$—COOH), 3.18 (m) (2H, C-2 protons), 4.08 (t) (2H, C-1 protons), 7.30–7.70 (m) (7H, C-5 and C-7 protons and phenyl protons), 7.98 (d) (1H, C-8 proton), 8.07 (t) (1H, —CH=), 10.31 (ds) (1H, —NHCO—).

By proceeding analogously the following alkyl esters and acids were prepared:

N-(3-benzylidene-9-oxo-1,2,3,9-tetrahydro-pyrrolo[2,1-b]quinazolin-6-yl)-aminocarbonyl-acetic acid, ethyl ester, m.p. 227°–229° C.;

N-(3-benzylidene-9-oxo-1,2,3,9-tetrahydro-pyrrolo[2,1-b]quinazolin-6-yl)-aminocarbonyl-acetic acid, m.p. 307°–310° C.;

(E)-3-[N-(3-benzylidene-9-oxo-1,2,3,9-tetrahydro-pyrrolo[2,1-b]quinazolin-6-yl)-aminocarbonyl]-2-propenoic acid, m.p. 315°–320° C.;

(E)-3-[N-(3-benzylidene-9-oxo-1,2,3,9-tetrahydro-pyrrolo[2,1-b]quinazolin-6-yl)-aminocarbonyl]-2-propenoic acid, ethyl ester, m.p. 298°–300° C.;

3-[N-(3-benzylidene-9-oxo-1,2,3,9-tetrahydro-pyrrolo[2,1-b]quinazolin-6-yl)-aminocarbonyl]-benzoic acid, methyl ester, m.p. 284°–287° C.;

3-[N-(3-benzylidene-9-oxo-1,2,3,9-tetrahydro-pyrrolo[2,1-b]quinazolin-6-yl)-aminocarbonyl]-benzoic acid, m.p. 384°–387° C.;

4-[N-(3-benzylidene-9-oxo-1,2,3,9-tetrahydro-pyrrolo[2,1-b]quinazolin-6-yl)-aminocarbonyl]-benzoic acid, methyl ester, m.p. 280°–285° C.;

4-[N-(3-benzylidene-9-oxo-1,2,3,9-tetrahydro-pyrrolo[2,1-b]quinazolin-6-yl)-aminocarbonyl]-benzoic acid, m.p. 310°–315° C.;

2-[N-(3-benzylidene-9-oxo-1,2,3,9-tetrahydro-pyrrolo[2,1-b]quinazolin-6-yl)-aminocarbonyl]-4,5-dichloro-benzoic acid, methyl ester;

3-benzylidene-6-N-ethoxycarbonyl-amino-1,2,3,9-tetrahydro-pyrrolo[2,1-b]quinazoline-9-one, m.p. 285°-288° C.;

3-benzylidene-6-N-methoxycarbonyl-amino-1,2,3,9-tetrahydro-pyrrolo[2,1-b]quinazoline-9-one;

2-[N-(3-benzylidene-9-oxo-1,2,3,9-tetrahydro-pyrrolo[2,1-b]quinazolin-6-yl)-aminocarbonyl]-4,5-dichloro-benzoic acid;

2-[N-(3-benzylidene-9-oxo-1,2,3,9-tetrahydro-pyrrolo[2,1-b]quinazolin-6-yl)-aminocarbonyl]propanoic acid, ethyl ester;

2-[N-(3-benzylidene-9-oxo-1,2,3,9-tetrahydro-pyrrolo[2,1-b]quinazolin-6-yl)-aminocarbonyl]-propanoic acid;

2-[N-(3-benzylidene-9-oxo-1,2,3,9-tetrahydro-pyrrolo[2,1-b]quinazolin-6-yl)-aminocarbonyl]-2-methyl-propanoic acid, ethyl ester;

2-[N-(3-benzylidene-9-oxo-1,2,3,9-tetrahydro-pyrrolo[2,1-b]quinazolin-6-yl)-aminocarbonyl]-2-methyl-propanoic acid;

2-[N-(3-benzylidene-9-oxo-1,2,3,9-tetrahydro-pyrrolo[2,1-b]quinazolin-6-yl)-aminocarbonyl]-butanoic acid, ethyl ester;

2-[N-(3-benzylidene-9-oxo-1,2,3,9-tetrahydro-pyrrolo[2,1-b]quinazolin-6-yl)-aminocarbonyl]-butanoic acid;

2-[N-(3-benzylidene-9-oxo-1,2,3,9-tetrahydro-pyrrolo[2,1-b]quinazolin-6-yl)-aminocarbonyl]-2-ethyl-butanoic acid, ethyl ester;

2-[N-(3-benzylidene-9-oxo-1,2,3,9-tetrahydro-pyrrolo[2,1-b]quinazolin-6-yl)-aminocarbonyl]-2-ethyl-butanoic acid;

2-[N-(3-benzylidene-9-oxo-1,2,3,9-tetrahydro-pyrrolo[2,1-b]quinazolin-6-yl)-aminocarbonyl]-2-phenyl-acetic acid, ethyl ester; and 2-[N-(3-benzylidene-9-oxo-1,2,3,9-tetrahydro-pyrrolo[2,1-b]quinazolin-6-yl)-aminocarbonyl]-2-phenyl-acetic acid.

EXAMPLE 3

6-amino-3-benzylidene-1,2,3,9-tetrahydro-pyrrolo[2,1-b]quinazoline-9-one (2 g) was reacted with phthalic anhydride (4.6 g) in tetrahydrofuran (150 ml) under stirring at the reflux temperature for 14 hours. After cooling the precipitate was filtered and washed with tetrahydrofuran and then with water to give 1.6 g of 2-[N-(3-benzylidene-9-oxo-1,2,3,9-tetrahydro-pyrrolo[2,1-b]quinazolin-6-yl)-aminocarbonyl]-benzoic acid, m.p. 302°-308° C., NMR (CDCl$_3$—CF$_3$COOD) δ ppm: 3.61 (bt) (2H, C-2 protons), 4.65 (t) (2H, C-1 protons), 7.4-8.0 (m) (7H; phenyl and C-4 and C-5 benzoyl protons), 8.0-8.5 (m) (6H; —CH=, C-5 and C-7 and C-8 protons, C-3 and C-6 benzoyl protons).

By proceeding analogously the following compounds were prepared:

cis-2-[N-(3-benzylidene-9-oxo-1,2,3,9-tetrahydro-pyrrolo[2,1-b]quinazolin-6-yl)-aminocarbonyl]-1-cyclohex-4-ene-carboxylic acid, m.p. 245°-248° C.;

2-[N-(3-benzylidene-9-oxo-1,2,3,9-tetrahydro-pyrrolo[2,1-b]quinazolin-6-yl)-aminocarbonyl]-cyclohex-1-ene-carboxylic acid;

cis-2-[N-(3-benzylidene-9-oxo-1,2,3,9-tetrahydro-pyrrolo[2,1-b]quinazolin-6-yl)-aminocarbonyl]-cyclohexane-carboxylic acid; and 2-[N-(3-benzylidene-9-oxo-1,2,3,9-tetrahydro-pyrrolo[2,1-b]quinazolin-6-yl)-aminocarbonyl]-3,4,5,6-tetrachloro-benzoic acid.

EXAMPLE 4

6-amino-3-benzylidene-1,2,3,9-tetrahydro-pyrrolo[2,1-b]quinazoline-9-one (3 g) was reacted with maleic anhydride (4.55 g) in tetrahydrofuran (220 ml) under stirring at the reflux temperature for 14 hours.

After cooling the precipitate was filtered and washed with tetrahydrofuran and then with water: crystallization from dimethylformamide gave 2.8 g of (Z)-3-[N-(3-benzylidene-9-oxo-1,2,3,9-tetrahydro-pyrrolo[2,1-b]quinazolin-6-yl)-aminocarbonyl]-2-propenoic acid, m.p. 210°-230° C., NMR (CDCl$_3$+CF$_3$COOD) δ ppm: 3.53 (m) (2H, C-2 protons), 4.57 (m) (2H, C-1 protons), 6.51 (d) (1H, α-propenoyl proton), 6.78 (d) (1H, β-propenoyl proton), 7.58 (broad peak) (5H, phenyl protons), 8.00-8.40 (m) (4H, —CH= and C-5, C-7 and C-8 protons); $J_{H\alpha H\beta}$=12.5 Hz.

By proceeding analogously the following compounds were prepared:

(Z)-3-[N-(3-benzylidene-9-oxo-1,2,3,9-tetrahydro-pyrrolo[2,1-b]quinazolin-6-yl)-aminocarbonyl]-2,3-dimethyl-2-propenoic acid;

4-[N-(3-benzylidene-9-oxo-1,2,3,9-tetrahydro-pyrrolo[2,1-b]quinazolin-6-yl)-aminocarbonyl]-butanoic acid;

5-[N-(3-benzylidene-9-oxo-1,2,3,9-tetrahydro-pyrrolo[2,1-b]quinazolin-6-yl)-aminocarbonyl]-pentanoic acid; and 4-[N-(3-benzylidene-9-oxo-1,2,3,9-tetrahydro-pyrrolo[2,1-b]quinazolin-6-yl)-aminocarbonyl]-3,3-dimethyl-butanoic acid.

EXAMPLE 5

6-amino-3-benzylidene-1,2,3,9-tetrahydro-pyrrolo[2,1-b]quinazoline-9-one (2 g) was reacted with 2,3-dichloro-maleic anhydride (3.46 g) in tetrahydrofuran (130 ml) under stirring at the reflux temperature for 3 hours. After cooling the solution was evaporated in vacuo to dryness: the residue was suspended in hot ethyl acetate and filtered. Crystallization from CH$_2$Cl$_2$-ethyl acetate gave 1 g of (Z)-3-[N-(3-benzylidene-9-oxo-1,2,3,9-tetrahydro-pyrrolo[2,1-b]quinazolin-6-yl)-aminocarbonyl]-2,3-dichloro-2-propenoic acid, m.p. 160°-165° C. (dec.), NMR (DMSO d6) δ ppm: 3.23 (m) (2p, C-2 protons), 4.14 (m) (2p, C-1 protons), 7.35-7.80 (m) (7H, C-5 and C-7 protons and phenyl protons), 8.07 (d) (1H, C-8 proton), 8.08 (bs) (1H, —CH=), 11.15 (s) (1H, CONH).

EXAMPLE 6

By proceeding according to Example 1, using suitable 6-amino-3-substituted benzylidene-1,2,3,9-tetrahydro-pyrrolo[2,1-b]quinazoline-9-ones, the following compounds were prepared:

N-[3-(2-methyl-benzylidene)-9-oxo-1,2,3,9-tetrahydro-pyrrolo[2,1-b]quinazolin-6-yl]-amino-oxoacetic acid, ethyl ester; m.p. 248°-251° C.;

N-[3-(3-methyl-benzylidene)-9-oxo-1,2,3,9-tetrahydro-pyrrolo[2,1-b]quinazolin-6-yl]-amino-oxoacetic acid, ethyl ester, m.p. 230°-233° C.;

N-[3-(4-methyl-benzylidene)-9-oxo-1,2,3,9-tetrahydro-pyrrolo[2,1-b]quinazolin-6-yl]-amino-oxoacetic acid, ethyl ester, m.p. 288°-290° C.;

N-[3-(2-methoxy-benzylidene)-9-oxo-1,2,3,9-tetrahydro-pyrrolo[2,1-b]quinazolin-6-yl]-amino-oxoacetic acid, ethyl ester, m.p. 260°-262° C.;

N-[3-(3-methoxy-benzylidene)-9-oxo-1,2,3,9-tetrahydro-pyrrolo[2,1-b]quinazolin-6-yl]-amino-oxoacetic acid, ethyl ester, m.p. 242°-244° C.;

N-[3-(4-methoxy-benzylidene)-9-oxo-1,2,3,9-tetrahydro-pyrrolo[2,1-b]quinazolin-6-yl]-amino-oxoacetic acid, ethyl ester, m.p. 265°-268° C.;

N-[3-(4-fluoro-benzylidene)-9-oxo-1,2,3,9-tetrahydro-pyrrolo[2,1-b]quinazolin-6-yl]-amino-oxoacetic acid, ethyl ester, m.p. 240°-243° C.;

N-[3-(2-chloro-benzylidene)-9-oxo-1,2,3,9-tetrahydro-pyrrolo[2,1-b]quinazolin-6-yl]-amino-oxoacetic acid, ethyl ester, m.p. 230°-233° C.;

N-[3-(2,3-dimethoxy-benzylidene)-9-oxo-1,2,3,9-tetrahydro-pyrrolo[2,1-b]quinazolin-6-yl]-amino-oxoacetic acid, ethyl ester, m.p. 170°-175° C.;

N-[3-(3,4-dimethoxy-benzylidene)-9-oxo-1,2,3,9-tetrahydro-pyrrolo[2,1-b]quinazolin-6-yl]-amino-oxoacetic acid, ethyl ester, m.p. 273°-275° C.;

N-[3-(4-nitro-benzylidene)-9-oxo-1,2,3,9-tetrahydro-pyrrolo[2,1-b]quinazolin-6-yl]-amino-oxoacetic acid, ethyl ester;

N-[3-(4-amino-benzylidene)-9-oxo-1,2,3,9-tetrahydro-pyrrolo[2,1-b]quinazolin-6-yl]-amino-oxoacetic acid, ethyl ester;

N-[3-(3-trifluoromethyl-benzylidene)-9-oxo-1,2,3,9-tetrahydro-pyrrolo[2,1-b]quinazolin-6-yl]-amino-oxoacetic acid, ethyl ester, m.p. 245°-250° C.;

N-[3-(3,4-methylenedioxy-benzylidene)-9-oxo-1,2,3,9-tetrahydro-pyrrolo[2,1-b]quinazolin-6-yl]-amino-oxoacetic acid, ethyl ester, m.p. 275°-280° C.;

N-[3-(2,5-dimethyl-benzylidene)-9-oxo-1,2,3,9-tetrahydro-pyrrolo[2,1-b]quinazolin-6-yl]-amino-oxoacetic acid, ethyl ester, m.p. 257°-259° C.;

N-[3-(2,4-dimethyl-benzylidene)-9-oxo-1,2,3,9-tetrahydro-pyrrolo[2,1-b]-quinazolin-6-yl]-amino-oxoacetic acid, ethyl ester;

N-[3-(2-ethoxy-benzylidene)-9-oxo-1,2,3,9-tetrahydro-pyrrolo[2,1-b]quinazolin-6-yl]-amino-oxoacetic acid, ethyl ester, m.p. 212°-214° C.;

N-[3-(3-ethoxy-benzylidene)-9-oxo-1,2,3,9-tetrahydro-pyrrolo[2,1-b]quinazolin-6-yl]-amino-oxoacetic acid, ethyl ester, m.p. 223°-226° C.;

N-[3-(4-ethoxy-benzylidene)-9-oxo-1,2,3,9-tetrahydro-pyrrolo[2,1-b]quinazolin-6-yl]-amino-oxoacetic acid, ethyl ester, m.p. 253°-256° C.;

N-[3-(4-chloro-benzylidene)-9-oxo-1,2,3,9-tetrahydro-pyrrolo[2,1-b]quinazolin-6-yl]-amino-oxoacetic acid, ethyl ester, m.p. 252°-255° C.;

N-[3-(3-chloro-benzylidene)-9-oxo-1,2,3,9-tetrahydro-pyrrolo[2,1-b]quinazolin-6-yl]-amino-oxoacetic acid, ethyl ester, m.p. 244°-247° C.;

N-[3-(2-methoxy-3-ethoxy-benzylidene)-9-oxo-1,2,3,9-tetrahydro-pyrrolo[2,1-b]quinazolin-6-yl]-amino-oxoacetic acid, ethyl ester, m.p. 212°-216° C.;

N-[3-(2,5-dimethoxy-benzylidene)-9-oxo-1,2,3,9-tetrahydro-pyrrolo[2,1-b]quinazolin-6-yl]-amino-oxoacetic acid, ethyl ester, m.p. 264°-267° C.;

N-[3-(3,5-dimethoxy-benzylidene)-9-oxo-1,2,3,9-tetrahydro-pyrrolo[2,1-b]quinazolin-6-yl]-amino-oxoacetic acid, ethyl ester;

N-[3-(2,4-dimethoxy-benzylidene)-9-oxo-1,2,3,9-tetrahydro-pyrrolo[2,1-b]quinazolin-6-yl]-amino-oxoacetic acid, ethyl ester;

N-[3-(3,4,5-trimethoxy-benzylidene)-9-oxo-1,2,3,9-tetrahydro-pyrrolo[2,1-b]quinazolin-6-yl]-amino-oxoacetic acid, ethyl ester, m.p. 285°-288° C.;

N-[3-(2,3,4-trimethoxy-benzylidene)-9-oxo-1,2,3,9-tetrahydro-pyrrolo[2,1-b]quinazolin-6-yl]-amino-oxoacetic acid, ethyl ester;

N-[3-(2-ethoxy-3-methoxy-benzylidene)-9-oxo-1,2,3,9-tetrahydro-pyrrolo[2,1-b]quinazolin-6-yl]-amino-oxoacetic acid, ethyl ester;

N-[3-(2,3-diethoxy-benzylidene)-9-oxo-1,2,3,9-tetrahydro-pyrrolo[2,1-b]quinazolin-6-yl]-amino-oxoacetic acid, ethyl ester, m.p. 174°-177° C.;

N-[3-(2-propoxy-benzylidene)-9-oxo-1,2,3,9-tetrahydro-pyrrolo[2,1-b]quinazolin-6-yl]-amino-oxoacetic acid, ethyl ester;

N-[3-(3-propoxy-benzylidene)-9-oxo-1,2,3,9-tetrahydro-pyrrolo[2,1-b]quinazolin-6-yl]-amino-oxoacetic acid, ethyl ester;

N-[3-(4-propoxy-benzylidene)-9-oxo-1,2,3,9-tetrahydro-pyrrolo[2,1-b]quinazolin-6-yl]-amino-oxoacetic acid, ethyl ester;

N-[3-(2-isopropoxy-benzylidene)-9-oxo-1,2,3,9-tetrahydro-pyrrolo[2,1-b]quinazolin-6-yl]-amino-oxoacetic acid, ethyl ester;

N-[3-(3-isopropoxy-benzylidene)-9-oxo-1,2,3,9-tetrahydro-pyrrolo[2,1-b]quinazolin-6-yl]-amino-oxoacetic acid, ethyl ester;

N-[3-(4-isopropoxy-benzylidene)-9-oxo-1,2,3,9-tetrahydro-pyrrolo[2,1-b]quinazolin-6-yl]-amino-oxoacetic acid, ethyl ester;

N-[3-(3,4-dichloro-benzylidene)-9-oxo-1,2,3,9-tetrahydro-pyrrolo[2,1-b]quinazolin-6-yl]-amino-oxoacetic acid, ethyl ester;

N-[3-(2,4-dichloro-benzylidene)-9-oxo-1,2,3,9-tetrahydro-pyrrolo[2,1-b]quinazolin-6-yl]-amino-oxoacetic acid, ethyl ester, m.p. 244°-246° C.;

N-[3-(2,6-dichloro-benzylidene)-9-oxo-1,2,3,9-tetrahydro-pyrrolo[2,1-b]quinazolin-6-yl]-amino-oxoacetic acid, ethyl ester, m.p. 234°-237° C.;

N-[3-(4-N,N-dimethylamino-benzylidene-9-oxo-1,2,3,9-tetrahydro-pyrrolo[2,1-b]quinazolin-6-yl]-amino-oxoacetic acid, ethyl ester;

N-[3-(2-methyl-benzylidene)-9-oxo-1,2,3,9-tetrahydro-pyrrolo[2,1-b]quinazolin-6-yl]-amino-oxoacetic acid, m.p. 235°-240° C. dec.;

N-[3-(3-methyl-benzylidene)-9-oxo-1,2,3,9-tetrahydro-pyrrolo[2,1-b]quinazolin-6-yl]-amino-oxoacetic acid, m.p. 232°-235° C.;

N-[3-(4-methyl-benzylidene)-9-oxo-1,2,3,9-tetrahydro-pyrrolo[2,1-b]quinazolin-6-yl]-amino-oxoacetic acid, m.p. 253°-256° C.;

N-[3-(2-methoxy-benzylidene)-9-oxo-1,2,3,9-tetrahydro-pyrrolo[2,1-b]quinazolin-6-yl]-amino-oxoacetic acid, m.p. 246°-248° C.;

N-[3-(3-methoxy-benzylidene)-9-oxo-1,2,3,9-tetrahydro-pyrrolo[2,1-b]quinazolin-6-yl]amino-oxoacetic acid, m.p. 195°-205° C. dec.;

N-[3-(4-methoxy-benzylidene)-9-oxo-1,2,3,9-tetrahydro-pyrrolo[2,1-b]quinazolin-6-yl]-amino-oxoacetic acid, m.p. 236°-240° C.;

N-[3-(4-fluoro-benzylidene)-9-oxo-1,2,3,9-tetrahydro-pyrrolo[2,1-b]quinazolin-6-yl]-amino-oxoacetic acid, m.p. 246°-248° C.;

N-[3-(2-chloro-benzylidene)-9-oxo-1,2,3,9-tetrahydro-pyrrolo[2,1-b]quinazolin-6-yl]-amino-oxoacetic acid, m.p. 300°-310° C. dec.;

N-[3-(2,3-dimethoxy-benzylidene)-9-oxo-1,2,3,9-tetrahydro-pyrrolo[2,1-b]quinazolin-6-yl]-amino-oxoacetic acid, m.p. 253°-255° C.;

N-[3-(3,4-dimethoxy-benzylidene)-9-oxo-1,2,3,9-tetrahydro-pyrrolo[2,1-b]quinazolin-6-yl]-amino-oxoacetic acid, m.p. 250°-260° C. (dec.);

N-[3-(2-methoxy-3-ethoxy-benzylidene)-9-oxo-1,2,3,9-tetrahydro-pyrrolo[2,1-b]quinazolin-6-yl]amino-oxoacetic acid, m.p. 228°-230° C. dec.;

N-[3-(2,5-dimethyl-benzylidene)-9-oxo-1,2,3,9-tetrahydro-pyrrolo[2,1-b]quinazolin-6-yl]amino-oxoacetic acid, m.p. 347°-349° C.;

N-[3-(2,4-dimethyl-benzylidene)-9-oxo-1,2,3,9-tetrahydro-pyrrolo[2,1-b]quinazolin-6-yl]-amino-oxoacetic acid;

N-[3-(2-ethoxy-benzylidene)-9-oxo-1,2,3,9-tetrahydro-pyrrolo[2,1-b]quinazolin-6-yl]-amino-oxacetic acid, m.p. 215°-220° C.;

N-[3-(3-ethoxy-benzylidene)-9-oxo-1,2,3,9-tetrahydro-pyrrolo[2,1-b]quinazoline-6-yl]-amino-oxoacetic acid, m.p. 238°-240° C.;

N-[3-(4-ethoxy-benzylidene)-9-oxo-1,2,3,9-tetrahydro-pyrrolo[2,1-b]quinazolin-6-yl]-amino-oxoacetic acid, m.p. 240°-245° C. dec.;

N-[3-(4-chloro-benzylidene)-9-oxo-1,2,3,9-tetrahydro-pyrrolo[2,1-b]quinazolin-6-yl]-amino-oxoacetic acid, m.p. 226°-229° C.;

N-[3-(3-chloro-benzylidene)-9-oxo-1,2,3,9-tetrahydro-pyrrolo[2,1-b]quinazolin-6-yl]-amino-oxoacetic acid, m.p. 236°-240° C.;

N-[3-(2,3,4-trimethoxy-benzylidene)-9-oxo-1,2,3,9-tetrahydro-pyrrolo[2,1-b]quinazolin-6-yl]-amino-oxoacetic acid;

N-[3-(2,4-dimethoxy-benzylidene)-9-oxo-1,2,3,9-tetrahydro-pyrrolo[2,1-b]quinazolin-6-yl]-amino-oxoacetic acid;

N-[3-(2-ethoxy-3-methoxy-benzylidene)-9-oxo-1,2,3,9-tetrahydro-pyrrolo[2,1-b]quinazolin-6-yl]-amino-oxoacetic acid;

N-[3-(2,3-diethoxy-benzylidene)-9-oxo-1,2,3,9-tetrahydro-pyrrolo[2,1-b]quinazolin-6-yl]-amino-oxoacetic acid, m.p. 220°-222° C.;

N-[3-(2-propoxy-benzylidene)-9-oxo-1,2,3,9-tetrahydro-pyrrolo[2,1-b]quinazolin-6-yl]-amino-oxoacetic acid;

N-[3-(3-propoxy-benzylidene)-9-oxo-1,2,3,9-tetrahydro-pyrrolo[2,1-b]quinazolin-6-yl]-amino-oxoacetic acid;

N-[3-(4-propoxy-benzylidene)-9-oxo-1,2,3,9-tetrahydro-pyrrolo[2,1-b]quinazolin-6-yl]-amino-oxoacetic acid;

N-[3-(3,4-dichloro-benzylidene)-9-oxo-1,2,3,9-tetrahydro-pyrrolo[2,1-b]quinazolin-6-yl]-amino-oxoacetic acid;

N-[3-(2,4-dichloro-benzylidene)-9-oxo-1,2,3,9-tetrahydro-pyrrolo[2,1-b]quinazolin-6-yl]-amino-oxoacetic acid, m.p. 205°-215° C. (dec.);

N-[3-(2,6-dichloro-benzylidene)-9-oxo-1,2,3,9-tetrahydro-pyrrolo[2,1-b]quinazolin-6-yl]-amino-oxoacetic acid, m.p. 222°-226° C.;

N-[3-(3,5-dimethoxy-benzylidene)-9-oxo-1,2,3,9-tetrahydro-pyrrolo[2,1-b]quinazolin-6-yl]-amino-oxoacetic acid;

N-[3-(2-isopropoxy-benzylidene)-9-oxo-1,2,3,9-tetrahydro-pyrrolo[2,1-b]quinazolin-6-yl]-amino-oxoacetic acid;

N-[3-(3-isopropoxy-benzylidene)-9-oxo-1,2,3,9-tetrahydro-pyrrolo[2,1-b]quinazolin-6-yl]-amino-oxoacetic acid;

N-[3-(4-isopropoxy-benzylidene)-9-oxo-1,2,3,9-tetrahydro-pyrrolo[2,1-b]quinazolin-6-yl]-amino-oxoacetic acid;

N-[3-(3,4-methylenedioxy-benzylidene)-9-oxo-1,2,3,9-tetrahydro-pyrrolo[2,1-b]quinazolin-6-yl]-amino-oxoacetic acid, m.p. 225°-229° C.;

N-[3-(4-nitro-benzylidene)-9-oxo-1,2,3,9-tetrahydro-pyrrolo[2,1-b]quinazolin-6-yl]-amino-oxoacetic acid;

N-[3-(4-amino-benzylidene)-9-oxo-1,2,3,9-tetrahydro-pyrrolo[2,1-b]quinazolin-6-yl]-amino-oxoacetic acid;

N-[3-(3-trifluoromethyl-benzylidene)-9-oxo-1,2,3,9-tetrahydro-pyrrolo[2,1-b]quinazolin-6-yl]-amino-oxoacetic acid, m.p. 250°-265° C. (dec.);

N-[3-(2,5-dimethoxy-benzylidene)-9-oxo-1,2,3,9-tetrahydro-pyrrolo[2,1-b]quinazolin-6-yl]-amino-oxoacetic acid, m.p. 238°-243° C. dec.;

N-[3-(3,4,5-trimethoxy-benzylidene)-9-oxo-1,2,3,9-tetrahydro-pyrrolo[2,1-b]quinazolin-6-yl]-amino-oxoacetic acid, m.p. 221°-225° C.;

N-[3-(4-methoxycarbonyl-benzylidene)-9-oxo-1,2,3,9-tetrahydro-pyrrolo[2,1-b]quinazolin-6-yl]-amino-oxoacetic acid, m.p. 282°-285° C.;

N-[3-(4-carboxy-benzylidene)-9-oxo-1,2,3,9-tetrahydro-pyrrolo[2,1-b]quinazolin-6-yl]-amino-oxoacetic acid, m.p. 240°-250° C. dec.; and N-[3-(4-N,N-dimethylamino-benzylidene)-9-oxo-1,2,3,9-tetrahydro-pyrrolo[2,1-b]quinazolin-6-yl]-amino-oxoacetic acid.

EXAMPLE 7

By proceeding according to Example 2, using suitable 6-amino-3-substituted benzylidene-1,2,3,9-tetrahydro-pyrrolo[2,1-b]quinazoline-9-ones, the following compounds were prepared:

N-[3-(3-methyl-benzylidene)-9-oxo-1,2,3,9-tetrahydro-pyrrolo[2,1-b]quinazolin-6-yl]-aminocarbonyl-acetic acid;

N-[3-(4-ethoxy-benzylidene)-9-oxo-1,2,3,9-tetrahydro-pyrrolo[2,1-b]quinazolin-6-yl]-aminocarbonyl-acetic acid;

N-[3-(4-methyl-benzylidene)-9-oxo-1,2,3,9-tetrahydro-pyrrolo[2,1-b]quinazolin-6-yl]-aminocarbonyl-acetic acid;

N-[3-(2-methoxy-benzylidene)-9-oxo-1,2,3,9-tetrahydro-pyrrolo[2,1-b]quinazolin-6-yl]-aminocarbonyl-acetic acid;

N-[3-(3-methoxy-benzylidene)-9-oxo-1,2,3,9-tetrahydro-pyrrolo[2,1-b]quinazolin-6-yl]-aminocarbonyl-acetic acid;

N-[3-(4-methoxy-benzylidene)-9-oxo-1,2,3,9-tetrahydro-pyrrolo[2,1-b]quinazolin-6-yl]-aminocarbonyl-acetic acid;

N-[3-(4-chloro-benzylidene)-9-oxo-1,2,3,9-tetrahydro-pyrrolo[2,1-b]quinazolin-6-yl]-aminocarbonyl-acetic acid;

N-[3-(2,6-dichloro-benzylidene)-9-oxo-1,2,3,9-tetrahydro-pyrrolo[2,1-b]quinazolin-6-yl]-aminocarbonyl-acetic acid;

N-[3-(2,3-dimethoxy-benzylidene)-9-oxo-1,2,3,9-tetrahydro-pyrrolo[2,1-b]quinazolin-6-yl]-aminocarbonyl-acetic acid;

N-[3-(2,5-dimethoxy-benzylidene)-9-oxo-1,2,3,9-tetrahydro-pyrrolo[2,1-b]quinazolin-6-yl]-aminocarbonyl-acetic acid;

3-{N-[3-(3-methyl-benzylidene)-9-oxo-1,2,3,9-tetrahydro-pyrrolo[2,1-b]quinazolin-6-yl]aminocarbonyl}-propanoic acid;

3-{N-[3-(4-ethoxy-benzylidene)-9-oxo-1,2,3,9-tetrahydro-pyrrolo[2,1-b]quinazolin-6-yl]-aminocarbonyl}-propanoic acid;
3-{N-[3-(4-methyl-benzylidene)-9-oxo-1,2,3,9-tetrahydro-pyrrolo[2,1-b]quinazolin-6-yl]-aminocarbonyl}-propanoic acid;
3-{N-[3-(2-methoxy-benzylidene)-9-oxo-1,2,3,9-tetrahydro-pyrrolo[2,1-b]quinazolin-6-yl]-aminocarbonyl}-propanoic acid;
3-{N-[3-(3-methoxy-benzylidene)-9-oxo-1,2,3,9-tetrahydro-pyrrolo[2,1-b]quinazolin-6-yl]-aminocarbonyl}-propanoic acid;
3-{N-[3-(4-methoxy-benzylidene)-9-oxo-1,2,3,9-tetrahydro-pyrrolo[2,1-b]quinazolin-6-yl]-aminocarbonyl}-propanoic acid;
3-{N-[3-(4-chloro-benzylidene)-9-oxo-1,2,3,9-tetrahydro-pyrrolo[2,1-b]quinazolin-6-yl]-aminocarbonyl}-propanoic acid;
3-{N-[3-(2,6-dichloro-benzylidene)-9-oxo-1,2,3,9-tetrahydro-pyrrolo[2,1-b]quinazolin-6-yl]-aminocarbonyl}-propanoic acid;
(E)-3-{N-[3-(3-methyl-benzylidene)-9-oxo-1,2,3,9-tetrahydro-pyrrolo[2,1-b]quinazolin-6-yl]-aminocarbonyl}-2-propenoic acid;
(E)-3-{N-[3-(3-ethoxy-benzylidene)-9-oxo-1,2,3,9-tetrahydro-pyrrolo[2,1-b]quinazolin-6-yl]-aminocarbonyl}-2-propenoic acid;
(E)-3-{N-[3-(4-methyl-benzylidene)-9-oxo-1,2,3,9-tetrahydro-pyrrolo[2,1-b]quinazolin-6-yl]-aminocarbonyl}-2-propenoic acid;
(E)-3-{N-[3-(2-methoxy-benzylidene)-9-oxo-1,2,3,9-tetrahydro-pyrrolo[2,1-b]quinazolin-6-yl]-aminocarbonyl}-2-propenoic acid;
(E)-3-{N-[3-(3-methoxy-benzylidene)-9-oxo-1,2,3,9-tetrahydro-pyrrolo[2,1-b]quinazolin-6-yl]-aminocarbonyl}-2-propenoic acid;
(E)-3-{N-[3-(4-methoxy-benzylidene)-9-oxo-1,2,3,9-tetrahydro-pyrrolo[2,1-b]quinazolin-6-yl]-aminocarbonyl}-2-propenoic acid;
(E)-3-{N-[3-(3-chloro-benzylidene)-9-oxo-1,2,3,9-tetrahydro-pyrrolo[2,1-b]quinazolin-6-yl]-aminocarbonyl}-2-propenoic acid;
(E)-3-{N-[3-(4-chloro-benzylidene)-9-oxo-1,2,3,9-tetrahydro-pyrrolo[2,1-b]quinazolin-6-yl]-aminocarbonyl}-2-propenoic acid;
(E)-3-{N-[3-(2,6-dichloro-benzylidene)-9-oxo-1,2,3,9-tetrahydro-pyrrolo[2,1-b]quinazolin-6-yl]-aminocarbonyl}-2-propenoic acid;
(E)-3-{N-[3-(4-ethoxy-benzylidene)-9-oxo-1,2,3,9-tetrahydro-pyrrolo[2,1-b]quinazolin-6-yl]-aminocarbonyl}-2-propenoic acid;
(E)-3-{N-[3-(2-chloro-benzylidene)-9-oxo-1,2,3,9-tetrahydro-pyrrolo[2,1-b]quinazolin-6-yl]-aminocarbonyl}-2-propenoic acid;
2-{N-[3-(3-methyl-benzylidene)-9-oxo-1,2,3,9-tetrahydro-pyrrolo[2,1-b]quinazolin-6-yl]-aminocarbonyl}-propanoic acid;
2-{N-[3-(4-ethoxy-benzylidene)-9-oxo-1,2,3,9-tetrahydro-pyrrolo[2,1-b]quinazolin-6-yl]-aminocarbony}-propanoic acid;
2-{N-[3-(4-methyl-benzylidene)-9-oxo-1,2,3,9-tetrahydro-pyrrolo[2,1-b]quinazolin-6-yl]-aminocarbony}-propanoic acid;
2-{N-[3-(2-methoxy-benzylidene)-9-oxo-1,2,3,9-tetrahydro-pyrrolo[2,1-b]quinazolin-6-yl]-aminocarbonyl}-propanoic acid;
2-{N-[3-(3-methoxy-benzylidene)-9-oxo-1,2,3,9-tetrahydro-pyrrolo[2,1-b]quinazolin-6-yl]-aminocarbonyl}-propanoic acid;
2-{N-[3-(4-methoxy-benzylidene)-9-oxo-1,2,3,9-tetrahydro-pyrrolo[2,1-b]quinazolin-6-yl]-aminocarbonyl}-propanoic acid;
2-{N-[3-(2,6-dichloro-benzylidene)-9-oxo-1,2,3,9-tetrahydro-pyrrolo[2,1-b]quinazolin-6-yl]-aminocarbonyl}-propanoic acid;
2-{N-[3-(4-chloro-benzylidene)-9-oxo-1,2,3,9-tetrahydro-pyrrolo[2,1-b]quinazolin-6-yl]-aminocarbonyl}-propanoic acid;
2-{N-[3-(3-methyl-benzylidene)-9-oxo-1,2,3,9-tetrahydro-pyrrolo[2,1-b]quinazolin-6-yl]-aminocarbonyl}-2-methyl-propanoic acid;
2-{N-[3-(4-ethoxy-benzylidene)-9-oxo-1,2,3,9-tetrahydro-pyrrolo[2,1-b]quinazolin-6-yl]-aminocarbonyl}-2-methyl-propanoic acid;
2-{N-[3-(4-methyl-benzylidene)-9-oxo-1,2,3,9-tetrahydro-pyrrolo[2,1-b]quinazolin-6-yl]-aminocarbonyl}-2-methyl-propanoic acid;
2-{N-[3-(2-methoxy-benzylidene)-9-oxo-1,2,3,9-tetrahydro-pyrrolo[2,1-b]quinazolin-6-yl]-aminocarbonyl}-2-methyl-propanoic acid;
2-{N-[3-(3-methoxy-benzylidene)-9-oxo-1,2,3,9-tetrahydro-pyrrolo[2,1-b]quinazolin-6-yl]-aminocarbonyl}-2-methyl-propanoic acid;
2-{N-[3-(4-methoxy-benzylidene)-9-oxo-1,2,3,9-tetrahydro-pyrrolo[2,1-b]quinazolin-6-yl]-aminocarbonyl}-2-methyl-propanoic acid;
2-{N-[3-(2,6-dichloro-benzylidene)-9-oxo-1,2,3,9-tetrahydro-pyrrolo[2,1-b]quinazolin-6-yl]-aminocarbonyl}-2-methyl-propanoic acid; and
2-{N-[3-(4-chloro-benzylidene)-9-oxo-1,2,3,9-tetrahydro-pyrrolo[2,1-b]quinazolin-6-yl]-aminocarbonyl}-2-methyl-propanoic acid.

EXAMPLE 8

By proceeding according to Example 3, using suitable 6-amino-substituted benzylidene-1,2,3,9-tetrahydro-pyrrolo[2,1-b]quinazoline-9-ones, the following compounds were prepared:
2-{N-[3-(3-methyl-benzylidene)-9-oxo-1,2,3,9-tetrahydro-pyrrolo[2,1-b]quinazolin-6-yl]-aminocarbonyl}-benzoic acid;
2-{N-[3-(3-ethoxy-benzylidene)-9-oxo-1,2,3,9-tetrahydro-pyrrolo[2,1-b]quinazolin-6-yl]-aminocarbonyl}-benzoic acid;
2-{N-[3-(4-methyl-benzylidene)-9-oxo-1,2,3,9-tetrahydro-pyrrolo[2,1-b]quinazolin-6-yl]-aminocarbonyl}-benzoic acid;
2-{N-[3-(2-methoxy-benzylidene)-9-oxo-1,2,3,9-tetrahydro-pyrrolo[2,1-b]quinazolin-6-yl]-aminocarbonyl}-benzoic acid;
2-{N-[3-(3-methoxy-benzylidene)-9-oxo-1,2,3,9-tetrahydrio-pyrrolo[2,1-b]quinazolin-6-yl]-aminocarbonyl}-benzoic acid;
2-{N-[3-(4-methoxy-benzylidene)-9-oxo-1,2,3,9-tetrahydro-pyrrolo[2,1-b]quinazolin-6-yl]-aminocarbonyl}-benzoic acid;
2-{N-[3-(4-ethoxy-benzylidene)-9-oxo-1,2,3,9-tetrahydro-pyrrolo[2,1-b]quinazolin-6-yl]-aminocarbonyl}-benzoic acid;
2-{N-[3-(4-chloro-benzylidene)-9-oxo-1,2,3,9-tetrahydro-pyrrolo[2,1-b]quinazolin-6-yl]-aminocarbonyl}-benzoic acid;

cis-2-{N-[3-(3-methyl-benzylidene)-9-oxo-1,2,3,9-tetrahydro-pyrrolo[2,1-b]quinazolin-6-yl]-aminocarbonyl}-1-cyclohex-4-ene-carboxylic acid;
cis-2-{N-[3-(3-ethoxy-benzylidene)-9-oxo-1,2,3,9-tetrahydro-pyrrolo[2,1-b]quinazolin-6-yl]-aminocarbonyl}-1-cyclohex-4-ene-carboxylic acid;
cis-2-{N-[3-(4-methyl-benzylidene)-9-oxo-1,2,3,9-tetrahydro-pyrrolo[2,1-b]quinazolin-6-yl]-aminocarbonyl}-1-cyclohex-4-ene-carboxylic acid;
cis-2-{N-[3-(2-methoxy-benzylidene)-9-oxo-1,2,3,9-tetrahydro-pyrrolo[2,1-b]quinazolin-6-yl]-aminocarbonyl}-1-cyclohex-4-ene-carboxylic acid;
cis-2-{N-[3-(3-methoxy-benzylidene)-9-oxo-1,2,3,9-tetrahydro-pyrrolo[2,1-b]quinazolin-6-yl]-aminocarbonyl}-1-cyclohex-4-ene-carboxylic acid;
cis-2-{N-[3-(4-methoxy-benzylidene)-9-oxo-1,2,3,9-tetrahydro-pyrrolo[2,1-b]quinazolin-6-yl]-aminocarbonyl}-1-cyclohex-4-ene-carboxylic acid;
cis-2-{N-[3-(4-ethoxy-benzylidene)-9-oxo-1,2,3,9-tetrahydro-pyrrolo[2,1-b]quinazolin-6-yl]-aminocarbonyl}-1-cyclohex-4-ene-carboxylic acid; and
cis-2-{N-[3-(4-chloro-benzylidene)-9-oxo-1,2,3,9-tetrahydro-pyrrolo[2,1-b]quinazolin-6-yl]-aminocarbonyl}-1-cyclohex-4-ene-carboxylic acid.

EXAMPLE 9

By proceeding according to Examples 4 and 5, using suitable 6-amino-3-substituted benzylidene-1,2,3,9-tetrahydro-pyrrolo[2,1-b]quinazolin-9-ones, the following compounds were prepared:

(Z)-3-{N-[3-(3-methyl-benzylidene)-9-oxo-1,2,3,9-tetrahydro-pyrrolo[2,1-b]quinazolin-6-yl]-aminocarbonyl}-2-propenoic acid;
(Z)-3-{N-[3-(3-ethoxy-benzylidene)-9-oxo-1,2,3,9-tetrahydro-pyrrolo[2,1-b]quinazolin-6-yl]-aminocarbonyl}-2-propenoic acid;
(Z)-3-{N-[3-(4-methyl-benzylidene)-9-oxo-1,2,3,9-tetrahydro-pyrrolo[2,1-b]quinazolin-6-yl]-aminocarbonyl}-2-propenoic acid;
(Z)-3-{N-[3-(2-methoxy-benzylidene)-9-oxo-1,2,3,9-tetrahydro-pyrrolo[2,1-b]quinazolin-6-yl]-aminocarbonyl}-2-propenoic acid;
(Z)-3-{N-[3-(3-methoxy-benzylidene)-9-oxo-1,2,3,9-tetrahydro-pyrrolo[2,1-b]quinazolin-6-yl]-aminocarbonyl}-2-propenoic acid;
(Z)-3-{N-[3-(4-methoxy-benzylidene)-9-oxo-1,2,3,9-tetrahydro-pyrrolo[2,1-b]quinazolin-6-yl]-aminocarbonyl}-2-propenoic acid;
(Z)-3-{N-[3-(4-ethoxy-benzylidene)-9-oxo-1,2,3,9-tetrahydro-pyrrolo[2,1-b]quinazolin-6-yl]-aminocarbonyl}-2-propenoic acid;
(Z)-2-{N-[3-(2,6-dichloro-benzylidene)-9-oxo-1,2,3,9-tetrahydro-pyrrolo[2,1-b]quinazolin-6-yl]-aminocarbonyl}-2-propenoic acid;
(Z)-3-{N-[3-(3-chloro-benzylidene)-9-oxo-1,2,3,9-tetrahydro-pyrrolo[2,1-b]quinazolin-6-yl]-aminocarbonyl}-2-propenoic acid;
(Z)-3-{N-[3-(4-chloro-benzylidene)-9-oxo-1,2,3,9-tetrahydro-pyrrolo[2,1-b]quinazolin-6-yl]-aminocarbonyl}-2-propenoic acid;
(Z)-3-{N-[3-(2-chloro-benzylidene)-9-oxo-1,2,3,9-tetrahydro-pyrrolo[2,1-b]quinazolin-6-yl]-aminocarbonyl}-2-propenoic acid;
(Z)-3-{N-[3-(2-methyl-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(3-methyl-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(4-methyl-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(2-methoxy-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(3-methoxy-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(4-methoxy-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(4-fluoro-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(2-chloro-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(2-ethoxy-3-methoxy-benzylidene)-9-oxo-1,2,3,9-tetrahydro-pyrrolo[2,1-]quinazolin-6-yl]-aminocarbonyl}-2,3-dichloro-2-propenoic acid;
(Z)-3-{N-[3-(2,3-diethoxy-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(3-chloro-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(4-chloro-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(3,4-methylenedioxy-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(2-ethoxy-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(3-ethoxy-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(4-ethoxy-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(2,6-dichloro-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(3,4-dichloro-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(4-nitro-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(4-amino-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(2-propoxy-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(3-propoxy-benzylidene)-9-oxo-1,2,3,9-tetrahydro-pyrrolo[2,1-b]quinazolin-6-yl]-aminocarbonyl}-2,3-dichloro-2-propenoic acid;
(Z)-3-{N-[3-(4-propoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(2-isopropoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(3-isopropoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(4-isopropoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(2,4-dichloro-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(2-methoxy-3-ethoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(3-N,N-dimethylamino-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(2,3,4-trimethoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(3,4,5-trimethoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(2,3-dimethoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(3,4-dimethoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(2,5-dimethoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(2,4-dimethoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(3,5-dimethoxy-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(2,5-dimethyl-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(2,4-dimethyl-benzylidene)-9-oxo-1,2,3,9-tetrahydro-pyrrolo[2,1-b]quinazolin-6-yl]-aminocarbonyl}-2,3-dichloro-2-propenoic acid;

(Z)-3-{N-[3-(3-trifluoromethyl-benzylidene)-9-oxo-1,2,3,9-tetrahydro-pyrrolo[2,1-b]quinazolin-6-yl]-aminocarbonyl}-2,3-dichloro-2-propenoic acid; and (Z)-3-[N-(3-benzylidene-1-methyl-9-oxo-1,2,3,9-tetrahydro-pyrrolo[2,1-b]quinazolin-6-yl)-aminocarbonyl]-2,3-dichloro-2-propenoic acid.

EXAMPLE 10

3-[N-(3-benzylidene-9-oxo-1,2,3,9-tetrahydro-pyrrolo[2,1-b]quinazolin-6-yl)-aminocarbonyl]-benzoic acid, methyl ester (0.85 g) dissolved in dimethylformamide (40 ml) was added to a suspension of 50% NaH (0.18 g) in dimethylformamide (5 ml) and the mixture was stirred at room temperature for 1 hour and then reacted with methyl iodide (0.54 g) at room temperature for 17 hours. The reaction mixture was diluted with ice water and then acidified with acetic acid: the precipitate was filtered and purified over a flash column using chloroform-ethyl acetate 3:1 as eluant. A further purification from isopropyl ether gave 3-[N-methyl-N-(3-benzylidene-9-oxo-1,2,3,9-tetrahydro-pyrrolo[2,1-b]quinazolin-6-yl)-aminocarbonyl]-benzoic acid, methyl ester, m.p. 200°–202° C. (0.42 g), which was dissolved in dimethylformamide (20 ml) and treated with 5% aqueous NaOH (3.6 ml) at room temperature for 2 hours. The precipitate, 3-[N-methyl-N-(3-benzylidene-9-oxo-1,2,3,9-tetrahydro-pyrrolo[2,1-b]quinazolin-6-yl)-aminocarbonyl]-benzoic acid, sodium salt, m.p. >300° C., was filtered and then dissolved in formic acid: the solution was diluted with water to give a precipitate which was filtered and washed with water until neutral. Crystallization from dichloromethane-methanol gave 0.2 g of 3-[N-methyl-N-(3-benzylidene-9-oxo-1,2,3,9-tetrahydro-pyrrolo[2,1-b]quinazolin-6-yl)-aminocarbonyl]-benzoic acid, m.p. 302°–304° C., NMR (CDCl$_3$) δ ppm.: 3.38 (m) (2H, C-2 protons), 3.61 (s) (3H, CH$_3$), 4.32 (t) (2H, C-1 protons), 7.14 (dd) (1H, C-7 proton), 7.32 (t) (1H, C-5 benzoyl proton), 7.35–7.85 (m) (7H, C-4 and C-6 benzoyl protons and phenyl protons), 7.88 (bs) (1H, —CH=), 8.00 (bd) (1H, C-5 proton), 8.13 (d) (1H, C-8 proton), 8.15 (bs) (1H, C-2 benzoyl proton).

By proceeding analogously the following compounds were prepared:

N-methyl-N-(3-benzylidene-9-oxo-1,2,3,9-tetrahydro-pyrrolo[2,1-b]quinazolin-6-yl)-amino-oxoacetic acid, NMR (CDCl$_3$) δ p.p.m.: 3.30 (m) (2H, C-2 protons), 3.45 (s) (3H, CH$_3$), 4.28 (t) (2H, C-1 protons), 7.2–7.6 (m) (7H; C-5, C-7 and phenyl protons), 7.85 (t) (1H,=CH—), 8.28 (d) (1H, C-8 proton).

N-ethyl-N-(3-benzylidene-9-oxo-1,2,3,9-tetrahydro-pyrrolo[2,1-b]quinazolin-6-yl)-amino-oxoacetic acid;

N-benzyl-N-(3-benzylidene-9-oxo-1,2,3,9-tetrahydro-pyrrolo[2,1-b]quinazolin-6-yl)-amino-oxoacetic acid;

N-methyl-N-(6-benzylidene-11-oxo-6,7,8,9-tetrahydro-11H-pyrido[2,1-b]quinazolin-3-yl)-amino-oxoacetic acid;

N-methyl-N-(3-benzylidene-9-oxo-1,2,3,9-tetrahydro-pyrrolo[2,1-b]quinazolin-6-yl)-aminocarbonyl-acetic acid;

3-[N-methyl-N-(3-benzylidene-9-oxo-1,2,3,9-tetrahydro-pyrrolo[2,1-b]quinazolin-6-yl)-aminocarbonyl]-propanoic acid;

(Z)-3-[N-methyl-N-(3-benzylidene-9-oxo-1,2,3,9-tetrahydro-pyrrolo[2,1-b]quinazolin-6-yl)-aminocarbonyl]-2-propenoic acid;

N-dichloromethyl-N-(3-benzylidene-9-oxo-1,2,3,9-tetrahydro-pyrrolo[2,1-b]quinazolin-6-yl)-amino-oxoacetic acid;

(Z)-3-[N-dichloromethyl-N-(3-benzylidene-9-oxo-1,2,3,9-tetrahydro-pyrrolo[2,1-b]quinazolin-6-yl)-aminocarbonyl]-2-propenoic acid;

(Z)-3-[N-ethyl-N-(3-benzylidene-9-oxo-1,2,3,9-tetrahydro-pyrrolo[2,1-b]quinazolin-6-yl)-aminocarbonyl]-2-propenoic acid;

(E)-3-[N-methyl-N-(3-benzylidene-9-oxo-1,2,3,9-tetrahydro-pyrrolo[2,1-b]quinazolin-6-yl)-aminocarbonyl]-2-propenoic acid;

2-[N-methyl-N-(3-benzylidene-9-oxo-1,2,3,9-tetrahydro-pyrrolo[2,1-b]quinazolin-6-yl)-aminocarbonyl]-propanoic acid; and (Z)-3-[N-methyl-N-(3-benzylidene-9-oxo-1,2,3,9-tetrahydro-pyrrolo[2,1-b]-quinazolin-6-yl)-aminocarbonyl]-2,3-dichloro-2-propenoic acid.

EXAMPLE 11

2-[N-(3-benzylidene-9-oxo-1,2,3,9-tetrahydro-pyrrolo[2,1-b]quinazolin-6-yl)aminocarbonyl]-benzoic acid (2 g) dissolved in hot dimethylformamide (30 ml) was treated with NaHCO$_3$ (0.4 g) dissolved in a little water for 30 minutes at room temperature. After dilution with ice water the precipitate was filtered and washed with water to give 1.8 g of 2-[N-(3-benzylidene-9-oxo-1,2,3,9-tetrahydro-pyrrolo[2,1-b]quinazolin-6-yl)-aminocarbonyl]-benzoic acid, sodium salt, m.p. >300° C.

By proceeding analogously the following compounds were prepared:

cis-2-[N-(3-benzylidene-9-oxo-1,2,3,9-tetrahydro-pyrrolo[2,1-b]quinazolin-6-yl)-aminocarbonyl]-1-cyclohex-4-ene-carboxylic acid, sodium salt, m.p. >300° C.;

(Z)-3-[N-(3-benzylidene-9-oxo-1,2,3,9-tetrahydro-pyrrolo[2,1-b]quinazolin-6-yl)-aminocarbonyl]-2-propenoic acid, sodium salt, m.p. >300° C.

EXAMPLE 12

(Z)-3-[N-(3-benzylidene-9-oxo-1,2,3,9-tetrahydro-pyrrolo[2,1-b]quinazolin-6-yl)-aminocarbonyl]-2-propenoic acid (1.22 g) was heated in anhydrous methanol (190 ml) containing boron trifluoride etherate (1.58 ml) at reflux temperature for 8 hours. The reaction mixture was concentrated to a small volume in vacuo and the precipitate was filtered and washed with water until neutral to give 1.1 g of (Z)-3-[N-(3-benzylidene-9-oxo-1,2,3,9-tetrahydro-pyrrolo[2,1-b]quinazolin-6-yl)-aminocarbonyl]-2-propenoic acid, methyl ester, m.p. 233°–235° C.

By proceeding analogously the following compounds were prepared:

(Z)-3-[N-(3-benzylidene-9-oxo-1,2,3,9-tetrahydro-pyrrolo[2,1-b]quinazolin-6-yl)-aminocarbonyl]-2-propenoic acid, ethyl ester;

3-[N-(3-benzylidene-9-oxo-1,2,3,9-tetrahydro-pyrrolo[2,1-b]quinazolin-6-yl)-aminocarbonyl]-propanoic acid, ethyl ester;

2-[N-(3-benzylidene-9-oxo-1,2,3,9-tetrahydro-pyrrolo[2,1-b]quinazolin-6-yl)-aminocarbonyl]-benzoic acid, ethyl ester; and (Z)-3-[N-(3-benzylidene-9-oxo-1,2,3,9-tetrahydro-pyrrolo[2,1-b]quinazolin-6-yl)-aminocarbonyl]-2,3-dichloro-2-propenoic acid, ethyl ester.

EXAMPLE 13

6-amino-3-benzylidene-1,2,3,9-tetrahydro-pyrrolo[2,1-b]quinazoline-9-one (2 g) was reacted with 3-piperidino-propionyl chloride, hydrochloride (3.66 g) in dimethylacetamide (120 ml) in the presence of pyridine (2.8 ml) at room temperature for 18 hours. The reaction mixture was then diluted with isopropyl ether (1 l) and the sticky precipitate was dissolved in water. After neutralization with $Na_2HPO_4$ the aqueous solution was extracted with chloroform: evaporation of the organic phase in vacuo to dryness and crystallization from chloroform-methanol gave 1.9 g of 3-benzylidene-6-N-(3-piperidino-propanoyl)-amino-1,2,3,9-tetrahydro-pyrrolo[2,1-b]quinazoline-9-one, m.p. 230°–234° C., NMR ($CDCl_3+CF_3COOD$) δ ppm.: 1.68 (m) (6H; C-3, C-4 and C-5 piperidinyl protons), 2.62 (m) (8H; C-2 and C-6 piperidinyl protons and —COCH$_2$CH$_2$N<), 3.72 (tt) (2H, C-2 protons), 4.22 (t) (C-1 protons), 7.28–7.62 (m) (5H, phenyl protons), 7.62 (dd) (1H, C-7 proton), 7.80 (t) (1H, —CH=), 7.90 (d) (1H, C-5 proton), 8.18 (1H, C-8 proton).

EXAMPLE 14

6-amino-3-benzylidene-1,2,3,9-tetrahydro-pyrrolo[2,1-b]quinazoline-9-one (2.3 g) was reacted with chloroacetyl chloride (1.35 g) in dimethylacetamide (100 ml) in the presence of pyridine (1.9 ml) at room temperature for 3 hours.

The reaction mixture was diluted with ice water and the precipitate was filtered and washed with water to give 3-benzylidene-6-N-chloroacetyl-amino-1,2,3,9-tetrahydro-pyrrolo[2,1-b]quinazoline-9-one, m.p. 281°–284° C. dec. (2.4 g), which was reacted with morpholine (0.63 g) in dimethylacetamide (90 ml) in the presence of anhydrous potassium carbonate (1 g) under stirring at 60° C. for 4 hours. After cooling the precipitate was filtered and washed with water: crystallization from acetone-ethanol gave 1.4 g of 3-benzylidene-6-N-morpholinoacetyl-amino-1,2,3,9-tetrahydro-pyrrolo[2,1-b]quinazoline-9-one, m.p. 223°–225° C., NMR ($CDCl_3$) δ ppm.: 2.70 (m) (4H, C-3 and C-5 morpholinyl protons), 3.23 (s) (2H, —CO—CH$_2$—N<), 3.28 (dt) (2H, C-2 protons), 3.82 (m) (4H, C-2 and C-6 morpholinyl protons), 4.25 (t) (2H, C-1 protons), 7.33–7.70 (m) (6H, C-7 proton and phenyl protons), 7.70–7.92 (m) (2H, =CH— and C-5 proton) 8.23 (d) (1H, C-8 proton).

By proceeding analogously the following compounds were prepared:

3-benzylidene-6-N-piperidinoacetyl-amino-1,2,3,9-tetrahydro-pyrrolo[2,1-b]quinazoline-9-one;

3-benzylidene-6-N-[(4-methyl-1-piperazinyl)-acetyl]-amino-1,2,3,9-tetrahydro-pyrrolo[2,1-b]quinazoline-9-one, m.p. 252°–254° C.;

3-benzylidene-6-N-[(1-pyrrolidinyl)-acetyl]-amino-1,2,3,9-tetrahydro-pyrrolo[2,1-b]quinazoline-9-one, m.p. 205°–207° C.;

3-benzylidene-6-N-[(1-piperazinyl)-acetyl]-amino-1,2,3,9-tetrahydro-pyrrolo[2,1-b]quinazoline-9-one;

3-benzylidene-6-N-(N',N'-diethylamino-acetyl)-amino-1,2,3,9-tetrahydro-pyrrolo[2,1-b]quinazoline-9-one, m.p. 191°–193° C.;

3-benzylidene-6-N-(N'-isopropylamino-acetyl)-amino-1,2,3,9-tetrahydro-pyrrolo[2,1-b]quinazoline-9-one;

3-benzylidene-6-N-[(4-ethoxycarbonyl-1-piperazinyl)-acetyl]-amino-1,2,3,9-tetrahydro-pyrrolo[2,1-b]quinazoline-9-one, m.p. 250°–252° C.;

3-benzylidene-6-N-(3-morpholino-propanoyl)-amino-1,2,3,9-tetrahydro-pyrrolo[2,1-b]quinazoline-9-one, m.p. 241°–244° C.;

3-benzylidene-6-N-[3-(1-pyrrolidinyl)-propanoyl]-amino-1,2,3,9-tetrahydro-pyrrolo[2,1-b]quinazoline-9-one;

3-benzylidene-6-N-[3-(4-methyl-1-piperazinyl)-propanoyl]-amino-1,2,3,9-tetrahydro-pyrrolo[2,1-b]quinazoline-9-one;

3-benzylidene-6-N-[3-(4-ethoxycarbonyl-1-piperazinyl)-propanoyl]-amino-1,2,3,9-tetrahydro-pyrrolo[2,1-b]quinazoline-9-one;

3-benzylidene-6-N-[3-(4-ethyl-1-piperazinyl)-propanoyl]-amino-1,2,3,9-tetrahydro-pyrrolo[2,1-b]quinazoline-9-one;

3-benzylidene-6-N-[3-(1-piperazinyl)-propanoyl]-amino-1,2,3,9-tetrahydro-pyrrolo[2,1-b]quinazoline-9-one; and 3-benzylidene-6-N-[(4-phenyl-1-piperazinyl)-acetyl]-amino-1,2,3,9-tetrahydro-pyrrolo[2,1-b]quinazoline-9-one.

EXAMPLE 15

By proceeding according to Example 14, starting from suitable substituted-benzylidene derivatives, the following compounds were prepared:

3-(2-methyl-benzylidene)-6-N-morpholinoacetyl-amino-1,2,3,9-tetrahydro-pyrrolo[2,1-b]quinazoline-9-one;

3-(3-methyl-benzylidene)-6-N-morpholinoacetyl-amino-1,2,3,9-tetrahydro-pyrrolo[2,1-b]quinazoline-9-one;

3-(4-methyl-benzylidene)-6-N-morpholinoacetyl-amino-1,2,3,9-tetrahydro-pyrrolo[2,1-b]quinazoline-9-one;

3-(2-methoxy-benzylidene)-6-N-morpholinoacetyl-amino-1,2,3,9-tetrahydro-pyrrolo[2,1-b]-quinazoline-9-one;

3-(3-methoxy-benzylidene)-6-N-morpholinoacetyl-amino-1,2,3,9-tetrahydro-pyrrolo[2,1-b]quinazoline-9-one;

3-(4-methoxy-benzylidene)-6-N-morpholinoacetyl-amino-1,2,3,9-tetrahydro-pyrrolo[2,1-b]quinazoline-9-one;

3-(4-fluoro-benzylidene)-6-N-morpholinoacetyl-amino-1,2,3,9-tetrahydro-pyrrolo[2,1-b]quinazoline-9-one;

3-(2-chloro-benzylidene)-6-N-morpholinoacetyl-amino-1,2,3,9-tetrahydro-pyrrolo[2,1-b]quinazoline-9-one;

3-(3-chloro-benzylidene)-6-N-morpholinoacetyl-amino-1,2,3,9-tetrahydro-pyrrolo[2,1-b]quinazoline-9-one;

3-(4-chloro-benzylidene)-6-N-morpholinoacetyl-amino-1,2,3,9-tetrahydro-pyrrolo[2,1-b]quinazoline-9-one;

3-(2-ethoxy-benzylidene)-6-N-morpholinoacetyl-amino-1,2,3,9-tetrahydro-pyrrolo[2,1-b]quinazoline-9-one;

3-(3-ethoxy-benzylidene)-6-N-morpholinoacetyl-amino-1,2,3,9-tetrahydro-pyrrolo[2,1-b]quinazolin-9-one;

3-(4-ethoxy-benzylidene)-6-N-morpholinoacetyl-amino-1,2,3,9-tetrahydro-pyrrolo[2,1-b]quinazoline-9-one;

3-(2,3-dimethoxy-benzylidene)-6-N-morpholinoactyl-amino-1,2,3,9-tetrahydro-pyrrolo[2,1-b]quinazoline-9-one;

3-(3,4-dichloro-benzylidene)-6-N-morpholinoacetyl-amino-1,2,3,9-tetrahydro-pyrrolo[2,1-b]quinazoline-9-one;

3-(2,5-dimethoxy-benzylidene)-6-N-morpholinoacetyl-amino-1,2,3,9-tetrahydro-pyrrolo[2,1-b]quinazoline-9-one;

3-(2-methoxy-3-ethoxy-benzylidene)-6-N-morpholinoacetyl-amino-1,2,3,9-tetrahydro-pyrrolo[2,1-b]quinazoline-9-one;

3-(2,6-dichloro-benzylidene)-6-N-morpholinoacetyl-amino-1,2,3,9-tetrahydro-pyrrolo[2,1-b]quinazoline-9-one;

3-(3-chloro-benzylidene)-6-N-(3-morpholino-propanoyl)-amino-1,2,3,9-tetrahydro-pyrrolo[2,1-b]quinazoline-9-one;

3-(3-methyl-benzylidene)-6-N-(3-morpholino-propanoyl)-amino-1,2,3,9-tetrahydro-pyrrolo[2,1-b]quinazoline-9-one;

3-(2,6-dichloro-benzylidene)-6-N-(3-morpholino-propanoyl)-amino-1,2,3,9-tetrahydro-pyrrolo[2,1-b]quinazoline-9-one;

3-(4-methyl-benzylidene)-6-N-(3-morpholino-propanoyl)-amino-1,2,3,9-tetrahydro-pyrrolo[2,1-b]quinazoline-9-one;

3-(4-chloro-benzylidene)-6-N-(3-morpholino-propanoyl)-amino-1,2,3,9-tetrahydro-pyrrolo[2,1-b]quinazoline-9-one;

3-(3-methoxy-benzylidene)-6-N-(3-morpholino-propanoyl)-amino-1,2,3,9-tetrahydro-pyrrolo[2,1-b]quinazoline-9-one;

3-(4-methoxy-benzylidene)-6-N-(3-morpholino-propanoyl)-amino-1,2,3,9-tetrahydro-pyrrolo[2,1-b]quinazoline-9-one;

3-(3-ethoxy-benzylidene)-6-N-(3-morpholino-propanoyl)-amino-1,2,3,9-tetrahydro-pyrrolo[2,1-b]quinazoline-9-one;

3-(4-ethoxy-benzylidene)-6-N-(3-morpholino-propanoyl)-amino-1,2,3,9-tetrahydro-pyrrolo[2,1-b]quinazoline-9-one;

3-(2-methyl-benzylidene)-6-N-[(4-methyl-1-piperazinyl)-acetyl]-amino-1,2,3,9-tetrahydro-pyrrolo[2,1-b]quinazoline-9-one;

3-(3-ethoxy-benzylidene)-6-N-[(4-methyl-1-piperazinyl)-acetyl]-amino-1,2,3,9-tetrahydro-pyrrolo[2,1-b]quinazoline-9-one;

3-(4-methyl-benzylidene)-6-N-[(4-methyl-1-piperazinyl)-acetyl]-amino-1,2,3,9-tetrahydro-pyrrolo[2,1-b]quinazoline-9-one;

3-(4-chloro-benzylidene)-6-N-[(4-methyl-1-piperazinyl)-acetyl]-amino-1,2,3,9-tetrahydro-pyrrolo[2,1-b]quinazoline-9-one;

3-(3-methoxy-benzylidene)-6-N-[(4-methyl-1-piperazinyl)-acetyl]-amino-1,2,3,9-tetrahydro-pyrrolo[2,1-b]quinazoline-9-one;

3-(4-methoxy-benzylidene)-6-N-[(4-methyl-1-piperazinyl)-acetyl]-amino-1,2,3,9-tetrahydro-pyrrolo[2,1-b]quinazoline-9-one;

3-(4-ethoxy-benzylidene)-6-N-[(4-methyl-1-piperazinyl)-acetyl]-amino-1,2,3,9-tetrahydro-pyrrolo[2,1-b]quinazoline-9-one; and 3-(2,6-dichloro-benzylidene)-6-N-[(4-methyl-1-piperazinyl)-acetyl]-amino-1,2,3,9-tetrahydro-pyrrolo[2,1-b]quinazoline-9-one.

EXAMPLE 16

6-N-trifluoroacetyl-amino-3-benzylidene-1,2,3,9-tetrahydro-pyrrolo[2,1-b]quinazoline-9-one, m.p. 320°–323° C., (1.8 g) was reacted with ethyl bromoacetate (2,4 g) in dimethylformamide (75 ml) in the presence of anhydrous potassium carbonate (1.95 g) under stirring at room temperature for 25 hours and then at 60° C. for 3 hours. After cooling, dilution with ice water and acidification with acetic acid, the precipitate was filtered and washed with water. Crystallization from CH$_2$Cl$_2$-methanol gave 6-N-ethoxycarbonylmethyl-amino-3-benzylidene-1,2,3,9-tetrahydro-pyrrolo[2,1-b]quinazoline-9-one, m.p. 222°–224° C., (1.2 g), which was dissolved in dimethylformamide (70 ml) and treated with 2N NaOH (7.5 ml) at room temperature for 3 hours. Dilution with acetone gave a precipitate, the N-carboxymethyl-amino-3-benzylidene-1,2,3,9-tetrahydro-pyrrolo[2,1-b]quinazoline-9-one, sodium salt, m.p.>300° C., which was filtered, dissolved in water and treated with acetic acid. Filtration of the precipitate and purification with acetic acid gave 0.6 g of 6-N-carboxymethyl-amino-3-benzylidene-1,2,3,9-tetrahydro-pyrrolo[2,1-b]quinazoline-9-one, m.p. 290°–293° C.

By processing analogously the following compounds were prepared:

6-N-(2-carboxy-ethyl)-amino-3-benzylidene-1,2,3,9-tetrahydro-pyrrolo[2,1-b]quinazoline-9-one;

6-N-carboxymethyl-amino-3-(3-methyl-benzylidene)-1,2,3,9-tetrahydro-pyrrolo[2,1-b]quinazoline-9-one;

6-N-carboxymethyl-amino-3-(3-ethoxy-benzylidene)-1,2,3,9-tetrahydro-pyrrolo[2,1-b]quinazoline-9-one;

6-N-carboxymethyl-amino-3-(4-methyl-benzylidene)-1,2,3,9-tetrahydro-pyrrolo[2,1-b]quinazoline-9-one;

6-N-carboxymethyl-amino-3-(4-ethoxy-benzylidene)-1,2,3,9-tetrahydro-pyrrolo[2,1-b]quinazoline-9-one;

6-N-carboxymethyl-amino-3-(3-methoxy-benzylidene)-1,2,3,9-tetrahydro-pyrrolo[2,1-b]quinazoline-9-one;

6-N-carboxymethyl-amino-3-(4-methoxy-benzylidene)-1,2,3,9-tetrahydro-pyrrolo[2,1-b]quinazoline-9-one;

6-N-carboxymethyl-amino-3-(2,6-dichloro-benzylidene)-1,2,3,9-tetrahydro-pyrrolo[2,1-b]quinazoline-9-one; and 6-N-carboxymethyl-amino-3-(4-chloro-benzylidene)-1,2,3,9-tetrahydro-pyrrolo[2,1-b]quinazoline-9-one.

EXAMPLE 17

N-(9-oxo-1,2,3,9-tetrahydro-pyrrolo[2,1-b]quinazolin-6-yl)-amino-oxoacetic acid, ethyl ester, m.p. 198°–200° C. (1.2 g) was reacted with benzaldehyde (0.84 g) in methanol (20 ml), in the presence of sodium methoxide (0.86 g) under stirring at 60° C. for 6 hours. After cooling the reaction mixture was concentrated in vacuo and diluted with ethyl ether: the precipitate was filtered, washed with ether and dissolved in water. Acidification with acetic acid gave a precipitate which was filtered and washed with water: crystallization from formic acid gave 0.4 g of N-(3-benzylidene-9-oxo-1,2,3,9-tetrahydro-pyrrolo[2,1-b]quinazolin-6-yl)-amino-oxoacetic acid, m.p. 220°–225° C.

EXAMPLE 18

6-nitro-1,2,3,9-tetrahydro-pyrrolo[2,1-b]quinazoline-9-one (10 g) was reacted with 4-carboxy-benzaldehyde (7.78 g) in methanol (400 ml) in the presence of sodium methoxide (8.2 g) under stirring at 60° C. for 7 hours.

After cooling the precipitate was filtered and washed with methanol then it was dissolved in water. The aqueous solution was acidified with acetic acid and the precipitate was filtered and washed with water: crystallization from dimethylformamide gave 3-(4-carboxy-benzylidene)-6-nitro-1,2,3,9-tetrahydro-pyrrolo[2,1-b]quinazoline-9-one, m.p. 299° C. dec. (7.6 g), which was suspended in dimethylformamide (1050 ml) and reacted with methyl iodide (6.7 g) in the presence of anhydrous $K_2CO_3$ (4.95 g) under stirring at room temperature for 3 hours. The reaction mixture was diluted with ice water and the precipitate was filtered and washed with water until neutral, to give 3-(4-methoxycarbonyl-benzylidene)-6-nitro-1,2,3,9-tetrahydro-pyrrolo[2,1-b]quinazoline-9-one, m.p. 264°–266° C. (7.8 g), which was reacted with $SnCl_2.2H_2O$ (23 g) in acetic acid (275 ml) and 35% HCl (53 ml) under stirring at 60° C. for 2.5 hours: after cooling the precipitate was filtered and washed with 2N HCl and water and finely dispersed in 2N NaOH. The precipitate was filtered and washed with water until neutral to give 6-amino-3-(4-methoxycarbonyl-benzylidene)-1,2,3,9-tetrahydro-pyrrolo[2,1-b]quinazoline-9-one, m.p. 292°–295° C. (5.9 g), which was treated with 35% HCl (120 ml) in acetic acid (240 ml) under stirring at 100° C. for 4 hours. After cooling the precipitate was filtered and washed with acetone to give 6-amino-3-(4-carboxy-benzylidene)-1,2,3,9-tetrahydro-pyrrolo[2,1-b]quinazoline-9-one, hydrochloride m.p. 295°–300° C. (5.2 g), which was suspended in water and treated with $Na_2HPO_4$ until pH 6: the precipitate was filtered and washed with water to give 6-amino-3-(4-carboxy-benzylidene)-1,2,3,9-tetrahydro-pyrrolo[2,1-b]quinazoline-9-one, m.p. 336°–339° C., (4.4 g) which was reacted with maleic anhydride (7.8 g) in dimethylacetamide (50 ml) at 100° C. for 6 hours. After cooling and dilution with ice water the precipitate was filtered and washed with water. Crystallization from dimethylformamide-methanol gave 3,2 g of (Z)-3-{N-[3-(4-carboxy-benzylidene)-9-oxo-1,2,3,9-tetrahydro-pyrrolo[2,1-b]quinazolin-6-yl]-aminocarbonyl}-2-propenoic acid, N.M.R. ($CDCl_3$—$CF_3COOD$) δ p.p.m.: 3.63 (m) (2H, C-2 protons), 4.68 (t) (2H, C-1 protons), 6.60 (d) and 6.83 (d) (2H, α- and β-propenoyl protons), 7.65–8.55 (m) (5H, —CH= and phenyl protons).

By proceeding analogously the following compound was prepared:

(Z)-3-{N-[3-(4-carboxy-benzylidene)-9-oxo-1,2,3,9-tetrahydro-pyrrolo[2,1-b]quinazolin-6-yl]-aminocarbonyl}-2,3-dichloro-2-propenoic acid.

EXAMPLE 19

(Z)-3-[N-(3-benzylidene-9-oxo-1,2,3,9-tetrahydro-pyrrolo[2,1-b]quinazolin-6-yl]-2-propenoic acid (1 g) was dissolved in chloroform (60 ml) and triethylamine (2.3 ml).

To the solution, at −10° C., ethyl chloroformate (1.6 ml) and then 2-(diethylamino)-ethanol (1.5 ml) were added dropwise. The reaction mixture was kept at 0° C. for 3 hours and then at room temperature for 20 hours.

After washing with water the organic solution was evaporated in vacuo to dryness: crystallization of the residue from diisopropyl ether gave 0.6 g of (Z)-3-[N-(3-benzylidene-9-oxo-1,2,3,9-tetrahydro-pyrrolo[2,1-b]quinazolin-6-yl)-aminocarbonyl]-2-propenoic acid, 2-(diethylamino)-ethyl ester.

By proceeding analogously the following compounds were prepared:

(Z)-3-[N-(3-benzylidene-9-oxo-1,2,3,9-tetrahydro-pyrrolo[2,1-b]quinazolin-6-yl)-aminocarbonyl]-2-propenoic acid, 2-(dimethylamino)-ethyl ester;

(E)-3-[N-(3-benzylidene-9-oxo-1,2,3,9-tetrahydro-pyrrolo[2,1-b]quinazolin-6-yl)-aminocarbonyl]-2-propenoic acid, 2-(diethylamino)-ethyl ester;

(Z)-3-[N-(3-benzylidene-9-oxo-1,2,3,9-tetrahydro-pyrrolo[2,1-b]quinazolin-6-yl)-aminocarbonyl]-2,3-dichloro-2-propenoic acid, 2-(diethylamino)-ethyl ester;

(E)-3-[N-(3-benzylidene-9-oxo-1,2,3,9-tetrahydro-pyrrolo[2,1-b]quinazolin-6-yl)-aminocarbonyl]-2-propenoic acid, 2-(dimethylamino)-ethyl ester;

(Z)-3-[N-(3-benzylidene-9-oxo-1,2,3,9-tetrahydro-pyrrolo[2,1-b]quinazolin-6-yl)-aminocarbonyl]-2,3-dichloro-2-propenoic acid, 2-(dimethylamino)-ethyl ester;

N-(3-benzylidene-9-oxo-1,2,3,9-tetrahydro-pyrrolo[2,1-b]quinazolin-6-yl)-amino-oxoacetic acid, 2-(diethylamino)-ethyl ester; and N-(3-benzylidene-9-oxo-1,2,3,9-tetrahydro-pyrrolo[2,1-b]quinazolin-6-yl)-amino-oxoacetic acid, 2-(dimethylamino)-ethyl ester.

EXAMPLE 20

Tablets, each weighing 200 mg and containing 100 mg of the active substance were manufactured as follows:

| Compositions (for 10,000 tablets) | |
|---|---|
| N—(3-benzylidene-9-oxo-1,2,3,9-tetrahydro-pyrrolo[2,1-b]quinazolin-6-yl)-amino-oxoacetic acid | 1000 g |
| Lactose | 710 g |
| Corn starch | 237.5 g |
| Talc powder | 37.5 g |

| -continued |  |
| --- | --- |
| Compositions (for 10,000 tablets) | |
| Magnesium stearate | 15 g |

N-(3-benzylidene-9-oxo-1,2,3,9-tetrahydro-pyrrolo[2,1-b]quinazolin-6-yl)-amino-oxoacetic acid, lactose and a half of the corn starch were mixed; the mixture was then forced through a sieve of 0.5 mm openings. Corn starch (18 g) was suspended in warm water (180 ml). The resulting paste was used to granulate the powder. The granules were dried, comminuted on a sieve of sieve size 1.4 mm, then the remaining quantity of starch, talc and magnesium stearate was added, carefully mixed and processed into tablets using punches of 8 mm diameter.

We claim:

1. A compound of general formula (I)

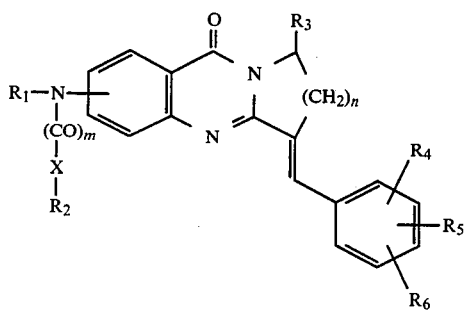 (1)

wherein
m represents 1;
n represents 1;
$R_1$ represents hydrogen or $C_1$-$C_6$ alkyl;
X completes a single bond or it represents:
 (a) a branched or straight $C_1$-$C_6$ alkylene or $C_2$-$C_6$ alkenylene chain unsubstituted or substituted by one or two halogen atoms;
 (b) phenylene,
$R_2$ represents:
 (a′) a group —$CH_2Z$, wherein Z represents chlorine, bromine or iodine;
 (b′) a group

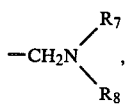

wherein each of $R_7$ and $R_8$ may be independently hydrogen or $C_1$-$C_6$ alkyl or $R_7$ and $R_8$, taken together with the nitrogen atom, form an unsubstituted N-pyrrolidinyl, morpholino or piperidino ring or a N-piperazinyl ring, which is unsubstituted or substituted by $C_1$-$C_4$ alkyl or by phenyl or by $C_1$-$C_2$ alkoxycarbonyl;
 (c′) carboxy or $C_1$-$C_7$ alkoxycarbonyl, unsubstituted or substituted by a group

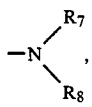

wherein $R_7$ and $R_8$ are $C_1$-$C_6$ alkyl;

where group $R_1$—N—(CO)$_m$—X—$R_2$ is attached at the 6-position of the pyrrolo[2,1-b]quinazoline ring system;
$R_3$ represents a hydrogen atom or a $C_1$-$C_6$ alkyl group;
each of $R_4$, $R_5$ and $R_6$ independently represents a hydrogen or a halogen atom, $C_1$-$C_6$ alkyl, halo-$C_1$-$C_4$ alkyl, $C_1$-$C_6$ alkoxy, carboxy, $C_1$-$C_7$ alkoxycarbonyl, nitro or a group

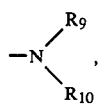

wherein each of $R_9$ and $R_{10}$ independently represents a hydrogen atom, a $C_1$-$C_6$ alkyl group, or any two adjacent $R_4$, $R_5$ and $R_6$, taken together, form a $C_1$-$C_3$ alkylenedioxy group, and the pharmaceutically acceptable salts thereof.

2. A compound of general formula (I)

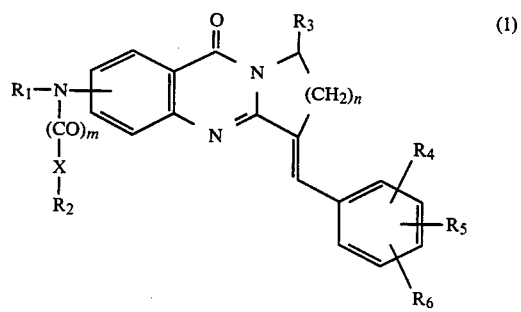 (1)

wherein
m represents 1;
n represents 1;
$R_1$ represents hydrogen;
X completes a single bond or it represents a branched or straight $C_1$-$C_6$ alkylene or $C_2$-$C_6$ alkylene chain;
$R_2$ represents a group

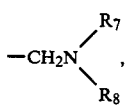

wherein $R_7$ and $R_8$, taken together with the nitrogen atom, form an unsubstituted N-pyrrolidinyl, morpholino or piperidine ring or a N-piperazinyl ring, which is unsubstituted or substituted by $C_1$-$C_4$ alkyl or by phenyl or by $C_1$-$C_2$ alkoxycarbonyl;
or $R_2$ represents carboxy or $C_1$-$C_7$ alkoxy-carbonyl;
where group $R_1$—N—(CO)$_m$—X—$R_2$ is attached to the 6-position of the pyrrolo[2,1-b]quinazoline ring system;
$R_3$ represents a hydrogen atom; each of $R_4$, $R_5$ and $R_6$ independently represents a hydrogen or a halogen atom, $C_1$-$C_6$ alkyl, halo-$C_1$-$C_4$ alkyl, $C_1$-$C_6$ alkoxy, and the pharmaceutical acceptable salts thereof.

3. N-(3-benzylidene-9-oxo-1,2,3,9-tetrahydro-pyrrolo[2,1-b]quinazolin-6-yl)-amino-oxoacetic acid, and the pharmaceutically acceptable salts and the $C_1$-$C_6$ alkyl esters thereof.

4. A compound selected from the group consisting of:
N-[3-(3-methyl-benzylidene)-9-oxo-1,2,3,9-tetrahydro-pyrrolo[2,1-b]quinazolin-6-yl]-amino-oxoacetic acid;

N-[3-(4-methyl-benzylidene)-9-oxo-1,2,3,9-tetrahydro-pyrrolo[2,1-b]quinazolin-6-yl]-amino-oxoacetic acid;
N-[3-(4-methoxy-benzylidene)-9-oxo-1,2,3,9-tetrahydro-pyrrolo[2,1-b]quinazolin-6-yl]-amino-oxoacetic acid;
N-[3-(3-ethoxy-benzylidene)-9-oxo-1,2,3,9-tetrahydro-pyrrolo[2,1-b]quinazolin-6-yl]-amino-oxoacetic acid;
N-[3-(4-ethoxy-benzylidene)-9-oxo-1,2,3,9-tetrahydro-pyrrolo[2,1-b]quinazolin-6-yl]-amino-oxoacetic acid;
N-[3-(4-fluoro-benzylidene)-9-oxo-1,2,3,9-tetrahydro-pyrrolo[2,1-b]quinazolin-6-yl]-amino-oxoacetic acid;
N-[3-(3-chloro-benzylidene)-9-oxo-1,2,3,9-tetrahydro-pyrrolo[2,1-b]quinazolin-6-yl]-amino-oxoacetic acid;
N-[3-(4-chloro-benzylidene)-9-oxo-1,2,3,9-tetrahydro-pyrrolo[2,1-b]quinazolin-6-yl]-amino-oxoacetic acid;
N-[3-(2,3-dimethoxy-benzylidene)-9-oxo-1,2,3,9-tetrahydro-pyrrolo[2;1-b]quinazolin-6-yl]-amino-oxoacetic acid;
N-[3-(2-methoxy-3-ethoxy-benzylidene)-9-oxo-1,2,3,9-tetrahydro-pyrrolo[2,1-b]quinazolin-6-yl]-amino-oxoacetic acid;
N-[3-(2,5-dimethoxy-benzylidene)-9-oxo-1,2,3,9-tetrahydro-pyrrolo[2,1-b]quinazolin-6-yl]-amino-oxoacetic acid;
N-[3-(2,5-dimethyl-benzylidene)-9-oxo-1,2,3,9-tetrahydro-pyrrolo[2,1-b]quinazolin-6-yl]-amino-oxoacetic acid;
N-[3-(2,6-dichloro-benzylidene)-9-oxo-1,2,3,9-tetrahydro-pyrrolo[2,1-b]quinazolin-6-yl]-amino-oxoacetic acid;
(Z)-3-[N-(3-benzylidene-9-oxo-1,2,3,9-tetrahydro-pyrrolo[2,1-b]quinazolin-6-yl)-aminocarbonyl]-2,3-dichloro-2-propenoic acid;
(E)-3-[N-(3-benzylidene-9-oxo-1,2,3,9-tetrahydro-pyrrolo[2,1-b]quinazolin-6-yl)-aminocarbonyl]-2-propenoic acid;
(Z)-3-[N-(3-benzylidene-9-oxo-1,2,3,9-tetrahydro-pyrrolo[2,1-b]quinazolin-6-yl)-aminocarbonyl]-2-propenoic acid;
N-[3-(2,4-dichloro-benzylidene)-9-oxo-1,2,3,9-tetrahydro-pyrrolo[2,1-b]quinazolin-6-yl]-amino-oxoacetic acid;
N-methyl-N-(3-benzylidene-9-oxo-1,2,3,9-tetrahydro-pyrrolo[2,1-b]quinazolin-6-yl)-amino-oxoacetic acid;
N-[3-(2-chloro-benzylidene)-9-oxo-1,2,3,9-tetrahydro-pyrrolo[2,1-b]quinazolin-6-yl]-amino-oxoacetic acid;
N-[3-(3-trifluoromethyl-benzylidene)-9-oxo-1,2,3,9-tetrahydro-pyrrolo[2,1-b]quinazolin-6-yl]-amino-oxoacetic acid;
N-[3-(3,4-dimethoxy-benzylidene)-9-oxo-1,2,3,9-tetrahydro-pyrrolo[2,1-b]quinazolin-6-yl]-amino-oxoacetic acid;
N-[3-(2,3-diethoxy-benzylidene)-9-oxo-1,2,3,9-tetrahydro-pyrrolo[2,1-b]quinazolin-6-yl]-amino-oxoacetic acid;
N-[3-(3,4,5-trimethoxy-benzylidene)-9-oxo-1,2,3,9-tetrahydro-pyrrolo[2,1-b]quinazolin-6-yl]-amino-oxoacetic acid;
N-[3-(3,4-dichloro-benzylidene)-9-oxo-1,2,3,9-tetrahydro-pyrrolo[2,1-b]quinazolin-6-yl]amino-oxoacetic acid;
N-[3-(4-carboxy-benzylidene)-9-oxo-1,2,3,9-tetrahydro-pyrrolo[2,1-b]quinazolin-6-yl]-amino-oxoacetic acid;
N-[3(3,4-methylenedioxy-benzylidene)-9-oxo-1,2,3,9-tetrahydro-pyrrolo[2,1-b]quinazolin-6-yl]-amino-oxoacetic acid;
N-(3-benzylidene-9-oxo-1,2,3,9-tetrahydro-pyrrolo[2,1-b]quinazolin-6-yl)-aminocarbonyl-acetic acid;
3-benzylidene-6-N-(3-morpholino-propionyl)-amino-1,2,3,9-tetrahydro-pyrrolo[2,1-b]quinazolin-9-one;
3-benzylidene-6-N-morpholinoacetyl-amino-1,2,3,9-tetrahydro-pyrrolo[2,1-b]quinazoline-9-one;
3-benzylidene-6-N-[(1-piperazinyl)-acetyl]-amino-1,2,3,9-tetrahydro-pyrrolo[2,1-b]quinazoline-9-one;
and the pharmaceutically acceptable salts and the $C_1$–$C_6$ alkyl esters thereof.

5. A pharmaceutical composition suitable for treating conditions of allergic origin, said composition comprising a suitable carrier and/or diluent and, as an active principle, a compound of the formula (I) according to claim 1, or a pharmaceutically acceptable salts thereof.

6. A method of preventing and/or treating conditions of allergic origin in a patient in need of such treatment, said method comprising administering to said patient an effective amount of a compound of a compound of claim 1.

7. A method of preventing and/or treating conditions of allergic origin in a patient in need of such treatment, said method comprising administering to said patient an effective amount of a pharmaceutical composition of claim 5.

* * * * *

UNITED STATES PATENT AND TRADEMARK OFFICE
CERTIFICATE OF CORRECTION

PATENT NO. : 4,579,847

DATED : April 1, 1986

INVENTOR(S) : G. Doria, C. Passaroti & M. L. Corno

It is certified that error appears in the above-identified patent and that said Letters Patent is hereby corrected as shown below:

Column 34, line 51 change "piperidine" to --piperidino--.

Signed and Sealed this

Twenty-fourth Day of February, 1987

Attest:

DONALD J. QUIGG

Attesting Officer  Commissioner of Patents and Trademarks